United States Patent [19]

Hawley-Nelson et al.

[11] Patent Number: 5,736,392
[45] Date of Patent: Apr. 7, 1998

[54] PEPTIDE-ENHANCED CATIONIC LIPID TRANSFECTIONS

[75] Inventors: Pamela Hawley-Nelson, Silver Spring; Jianqing Lan, Germantown; PoJen Shih, Columbia; Joel A. Jessee, Mt. Airy; Kevin P. Schifferli, Germantown, all of Md.

[73] Assignee: Life Technologies, Inc., Rockville, Md.

[21] Appl. No.: 658,130

[22] Filed: Jun. 4, 1996

Related U.S. Application Data

[63] Continuation-in-part of Ser. No. 477,354, Jun. 7, 1995, abandoned.
[51] Int. Cl.$^6$ .................. C12N 15/00; C07K 14/005; G01N 33/92
[52] U.S. Cl. .................. 435/320.1; 435/172.3; 436/71; 530/350
[58] Field of Search .................. 435/320.1, 172.3; 436/71; 530/350

[56] References Cited

U.S. PATENT DOCUMENTS

| | | | |
|---|---|---|---|
| 4,946,787 | 8/1990 | Eppstein et al. | 264/4.1 |
| 5,166,320 | 11/1992 | Wu et al. | 530/395 |
| 5,354,844 | 10/1994 | Beug et al. | 530/345 |
| 5,574,142 | 11/1996 | Meyer, Jr. et al. | 536/23.1 |
| 5,589,392 | 12/1996 | Short | 435/320.1 |

FOREIGN PATENT DOCUMENTS

| | | |
|---|---|---|
| B-26526/92 | 9/1992 | Australia. |
| 0 359 347 | 3/1990 | European Pat. Off.. |
| 0 544 292 A2 | 11/1992 | European Pat. Off.. |
| WO91/16024 | 10/1991 | WIPO. |
| 92/13570 | 8/1992 | WIPO. |
| WO 93/07282 | 4/1993 | WIPO. |
| WO 93/07283 | 4/1993 | WIPO. |
| WO93/19768 | 10/1993 | WIPO. |
| WO94/23751 | 10/1994 | WIPO. |
| 95/02397 | 1/1995 | WIPO. |
| WO95/31557 | 11/1995 | WIPO. |
| WO96/01841 | 1/1996 | WIPO. |
| WO96/05218 | 2/1996 | WIPO. |
| WO96/10038 | 4/1996 | WIPO. |

OTHER PUBLICATIONS

Kamata et al. Amphiphilic peptides enhance the efficiency of liposome-mediated DNA transfection Nucleic Acids Res. vol. 22 pp. 536–537, 1994.
Life Technologies Catalog 1993 pp. 9–19.
Grant, D.S. et al. (1989), "Two Different Laminin Domains Mediate the Differentiation of Human Endothelial Cells into Capillary-like Structures In Vitro," *Cell* 58:933–943.
Gardner, J.M. and Hynes, R.O. (1985), "Interaction of Fibronectin with Its Receptor on Platelets," *Cell* 42:439–448.
Wickham, T.J. et al. (1995), "Targeting of adenovirus penton base to new receptors through replacement of its RGD motif with other receptor–specific peptide motifs," *Gene Therapy* 2:750–756.

Pierschbacher, M.D. and Ruoslahti, E. (1987), "Influence of Stereochemistry of the Sequence Arg–Gly–Asp–Xaa on Binding Specificity in Cell Adhesion," *J. Biol. Chem.* 262(36):17294–17298.
Mason, P.W. et al. (1994), "RGD sequence of foot-and-mouth disease virus is essential for infecting cells via the natural receptor but can be bypassed by an antibody–dependent enhancement pathway," *Proc. Natl. Acad. Sci. USA* 91:1932–1936.
Ruoslahti, E. and Pierschbacher, M.D. (1987), "New Perspectives in Cell Adhesion: RGD and Integrins," *Science* 238:491–497.
Pierschbacher, M.D. and Ruoslahti, E. (1984), "Cell attachment activity of fibronectin can be duplicated by small synthetic fragments of the molecule," *Nature* 309:30–33.
Dedhar, S. et al. (1987), "A Cell Surface Receptor Complex for Collagen Type I Recognizes the Arg–Gly–Asp Sequence," *J. Cell Biol.* 104:585–593.
Friedlander, D.R. et al. (1988), "Functional Mapping of Cytotactin: Proteolytic Fragments Active in Cell–Substrate Adhesion," *J. Cell Biol.* 107:2329–2340.
Humphries, M.J. et al. (1986), "Identification of an Alternatively Spliced Site in Human Plasma Fibronectin That Mediates Cell Type–specific Adhesion," *J. Cell Biol.* 103:2637–2647.
Suzuki, S. et al. (1985), "Complete amino acid sequence of human vitronectin deduced from cDNA. Similarity of cell attachment sites in vitronectin and fibronectin," *EMBO J.* 4(10):2519–2524.
Wayner, E.A. et al. (1989), "Identification and Characterization of the T Lymphocyte Adhesion Receptor for an Alternative Cell Attachment Domain (CS–1) in Plasma Fibronectin," *J. Cell Biol.* 109:1321–1330.
Lawler, J. et al. (1988), "Cell Attachment to Thrombospondin: The Role of ARG–GLY–ASP, Calcium, and Integrin Receptors," *J. Cell Biol.* 107:2351–2361.
Haverstick, D.M. et al. (1986), "Inhibition of Platelet Adhesion to Fibronectin, Fibrinogen, and von Willebrand Factor Substrates by a Synthetic Tetrapeptide Derived From the Cell–Binding Domain of Fibronectin," *Blood* 86(4):946–952.
Humphries, M.J. et al. (1987), "Identification of Two Distinct Regions of the Type III Connecting Segment of Human Plasma Fibronectin That Promote Cell Type–specific Adhesion," *J. Biol. Chem.* 262(14):6886–6892.

(List continued on next page.)

*Primary Examiner*—James Ketter
*Assistant Examiner*—John S. Brusca
*Attorney, Agent, or Firm*—Greenlee, Winner & Sullivan, P.C.

[57] ABSTRACT

The present invention discloses compositions useful for transfecting eukaryotic cells comprising nucleic acid complexes with peptides, proteins or protein fragments, wherein the peptide is optionally covalently coupled to a DNA-binding group, and cationic lipids useful for transfecting eukaryotic cells. Methods for the preparation of transfecting compositions and use as intracellular delivery agents and extracellular targeting agents are also disclosed.

34 Claims, 8 Drawing Sheets

OTHER PUBLICATIONS

Zhou, X. and Huang, L. (1994), "DNA transfection mediated by cationic liposomes containing lipopolylysine: characterization and mechanism of action," *Biochim. Biophys. Acta* 1189:195–203.

Stegmann, T. et al. (1989), "Protein–mediated membrane fusion," *Ann. Rev. Biophys. Biophys. Chem.* 18:187–211.

Aumailley, M. et al. (1989), "Cell Attachment Properties of Collagen Type VI and Arg–Gly–Asp Dependent Binding to its α2(VI) and α3(VI) Chains," *Exp. Cell Res.* 181:463–474.

DeRoberts et al., "Intracellular migration of nuclear proteins in Xenopus oocytes," *Nature* 272:254–256 (1978).

Väänänen et al., "Fusion and Haemolysis of Erythrocytes Caused by Three Togaviruses: Semiki Forest, Sindbis, and Rubella," *J. Gen. Virology* (1980), 46: 467–475.

Carrasco, L. et al. "Modification of Membrane Permeability in Vaccinia Virus–Infected Cells," (1982), *J. Virol.* 117:62–69.

Eytan, G.D., "Use of Lipsomes for Reconstitution of Biological Functions," *Biochem. Biphys. Acata* (1982) 694:185–202.

Young et al., "Interaction of Enveloped Viruses with Planar Bilayer Membranes: Observations on Sendai, Influenza, Vesicular Stomatitis, and Simiki Forest Viruses," *Virology* (1983) 128:186–194.

Marsh et al., "Interactions of Simiki Forest Virus Spike Glycoprotein Rosettes and Vesicles with Cultured Cells," *J. Cell Biol.* (1983) 96:455–461.

Schlegel, R. et al., "Inhibition of VSV Binding and Infectivity by Phosphatidylserine: Is Phosphatidylserine a VSV–Binding Site?" *Cell* 32:639–646 (1983).

Kalderon et al., "A Short Amino Acid Sequence Able to Specify Nuclear Location," *Cell* 39:499–509 (1984).

Kraaijeveld, S.A. et al., "The effect of liposomal charge on the neutralizing antibody response against inactivated encephalomyocarditis and Simiki Forest Viruses," *Clin. Exp. Immunol.*, (1984)56:509–514.

Schlegel, R. and M. Wade, "Biologically Active Peptides of the Vesicular Stomatitus Virus Glycoprotein," *J. Virol.* 53(1):319–323 (1985).

Klappe, K. et al., "Parameters Affecting Fusion between Sendai Virus and Liposomes. Role of Viral Proteins, Liposome Composition, and pH," *Biochemistry* (1986) 25:8252–8260.

Sands, J.A., "Virucidal activity of cetyltrimethylammonium bromide below the critical micelle concentration," *FEMS Microbiol. Lett.* (1986) 36:261–263.

Scheule, "Novel Preparation of Functional Sindbis Virosomes," *Biochemistry* (1986) 25:4223–4232.

Lanford et al., "Induction of Nuclear Transport with a Synthetic Peptide Homologous to the SV40 T Antigen Transport Signal," *Cell* 46:575–582 (1986).

Kaneda et al., "The Improved Efficient Method for Introducing Macromolecules into Cells Using HVJ (Sendai virus) Liposomes with Gangliosides," *Exp. Cell Res.* (1987) 173:56–69.

Otero, M.J., and Carrasco, L. "Proteins are Cointernalized with Virion Particles during Early Infection," (1987), *J. Virol.* 160:75–80.

Tikchonenko, T., et al., (1988) "Transfer of condensed viral DNA into eukaryotic cells using proteoliposomes," *Gene* 63:321–330.

Gould–Fogerite, S. et al., "Chimerasome–mediated gene transfer in vitro and in vivo," (1989) *Gene* 84:429–438.

Kaneda et al., "Introduction and Expression of the Human Insulin Gene in Adult Rat Liver," *J. Biol. Chem.* (1989) 264(21):1216–1219.

Neugebauer, J. "Detergents: An Overview," *Meth.Enzymol.*, (1990) 182:239–253.

Lapidot et al., "Fusion–Mediated Microinjection of Liposome–Enclosed DNA into Cultured Cells with the Aid of Influenza Virus Glycoproteins," *Experimental Cell Research* (1990) 189:241–246.

Konopka, K. et al., "Enhancement of human immunodeficiency virus type 1 infection by cationic liposomes: the role of CD4, serum and liposome–cell interactions," *J. Gen. Virol.* (1991) 72:2685–2696.

Curiel, D.T. et al. "Adenovirus enhancement of transferrin–polylysine–mediated gene delivery," (1991) *Proc. Natl. Acad. Sci. USA* 88:8850–8854.

Liljistrom, P. and Garoff, H. "A New Generation of Animal Cell Expression Vectors Based on the Semliki Forest Virus Replicon," (1991) *Biotech.* 9:1356–1361.

Phalen et al., "Cholesterol is Required for Infection by Semiki Forest Virus," *J. Cell Biology* (1991) 112(4):615–623.

Murata et al., "Modification of the N–Terminus of Membrane Fusion–Active Peptides Blocks the Fusion Activity," *Biochem. and Biophys. Res. Communications* (1991) 179(2):1050–1055.

Cotten et al., (1992) "High–efficiency receptor–mediated delivery of small and large 48 kilobase gene constructs using the endosome–disruption activity of defective or chemically inactivated adenovirus particles," *Proc. Natl. Acad. Sci. USA* 89:6094–6098.

Curiel, D.T. et al., (1992) "High–Efficiency Gene Transfer Mediated by Adenovirus Coupled to DNA–Polylysine Complexes," *Hum. Gene. Therapy* 3:147–154.

Wagner, E. et al., (1992) "Coupling of adenovirus to transferrin–polylysine/DNA complexes greatly enhances receptor–mediated gene delivery and expression of transfected genes," *Proc. Natl. Acad. Sci. USA* 89:6099–6103.

Wagner, E. et al., (1992) "Influenza virus hemagglutinin HA–2 N–terminal fusogenic peptides augment gene transfer by transferrin–polylysine–DNA complexes: Toward a synthetic virus–like gene–transfer vehicle," *Proc. Natl. Acad. Sci. USA* 89:7934–7938.

Epand et al, "Peptide models for the membrane destabilzing actions of viral fusion proteins," *Biopolymers* 32:309 (1992).

Walker et al., "Cationic lipids direct a viral glycoprotein into the clas I major histocompatibility complex antigen–presentation pathway," *Proc. Natl. Acad. Sci. USA* (1992) 89:7915–7918.

Ciccarone et al., "Cationic Liposome–Mediated Transfection of Eukaryotic Cells: High Efficiency Nucleic Acid Delivery with Lipofectin, Lipofectace™, and Lipofectamine™ Reagents," *Faseb J.*, Abstracts, (1993) 7(7):A1131, Abstract No. 454.

Yoshimura et al. "Adenovirus–mediated Augmentation of Cell Transfection with Unmodified Plasmid Vectors," *J. Biol. Chem.* 268:2300 (1993).

"Transfection Reagent," *Genetic Engineering News* (15 Jun. 1993), p.12, col. 4.

Remy et al., "Targeted gene transfer into hepatoma cells with lipopolyamine–condensed DNA particles presenting galactose ligands: A stage toward artificial viruses," *Proc. Natl. Acad. Sci., USA* 92:1744–1748 (1995).

PEPTIDE-ENHANCED CATIONIC LIPID TRANSFECTIONS

CROSS-REFERENCE TO RELATED APPLICATIONS

This application is a Continuation-in-Part of U.S. application Ser. No. 08/477,354, filed Jun. 7, 1995, now abandoned, which is incorporated by reference in its entirety herein.

FIELD OF THE INVENTION

Compositions containing peptides, optionally conjugated to DNA-binding groups, and cationic lipids useful for transfecting eukaryotic cells are disclosed. Also disclosed are methods of transfecting eukaryotic cells employing such compositions.

BACKGROUND OF THE INVENTION

Lipid aggregates such as liposomes can function to facilitate introduction of macromolecules, such as DNA, RNA, and proteins, into living cells. Lipid aggregates comprising cationic lipid components can be effective for delivery and introduction of large anionic molecules, such as nucleic acids, into certain types of cells. See Felgner, P. L. and Ringold, G. M. (1989) Nature 337:387–388 and Felgner, P. L. et al. (1987) Proc. Natl. Acad. Sci. U.S.A. 84:7413. Since the membranes of most cells have a net negative charge, anionic molecules, particularly those of high molecular weight, are not readily taken up by cells. Cationic lipids aggregate to and bind polyanions, such as nucleic acids, tending to neutralize the negative charge. The effectiveness of cationic lipids in transfection of nucleic acids into cells is thought to result from an enhanced affinity of cationic lipid-nucleic acid aggregates for cells, as well as the function of the lipophilic components in membrane fusion.

Cationic lipids are not universally effective for transfection of all cell types. Effectiveness of transfection of different cells depends on the particular cationic lipid composition and the type of lipid aggregate formed. In general, polycationic lipids are more efficient than monocationic lipids in transfecting eukaryotic cells. Behr, J-P. et al. (1989) Proc. Natl. Acad. Sci. 86:6982–6986, Hawley-Nelson, P., et al. (1993) FOCUS 15:73 and U.S. Pat. No. 5,334,761 (Gebeyehu et al.). Behr et al. and EPO published application 304 111 (1990), for example, describe improved transfection using carboxyspermine-containing cationic lipids including 5-carboxyspermylglycine dioctadecyl-amide (DOGS) and dipalmitoylphosphatidylethanolamine 5-carboxyspermylamide (DPPES). Despite their relative effectiveness, however, successful transfection of eukaryotic cell cultures using polycationic lipid reagents requires high dosages of nucleic acid (approximately $10^5$ DNA molecules per cell).

Many biological materials are taken up by cells by receptor-mediated endocytosis. See: Pastan and Willingham (1981) Science 214:504–509. This mechanism involves binding of a ligand to a cell-surface receptor, clustering of ligand-bound receptors, and formation of coated pits followed by internalization of the ligands into endosomes. Both enveloped viruses, like influenza virus and alphaviruses, and non-enveloped viruses, like Adenovirus, infect cells via endocytotic mechanisms. See: Pastan, I. et al. (1986) in *Virus Attachment and Entry into Cells*, (Crowell, R. L. and Lonberg-Holm, K., eds.) Am. Soc. Microbiology, Washington, p. 141–146; Kielian, M. and Helenius, A. (1986) "Entry of Alphaviruses" in *The Togaviridae and Flaviviridae*, (Schlesinger, S. and Schlesinger, M. J., eds.) Plenum Press, New York p.91–119; FitzGerald, D. J. P. et al. (1983) Cell 32:607–617.

The introduction of foreign DNA sequences into eukaryotic cells mediated by viral infection is generally orders of magnitude more efficient than transfection with cationic lipid reagents. Viral infection of cell cultures requires fewer than 10 virus particles per cell. Although the detailed mechanism of fusion is not fully understood and varies among viruses, viral fusion typically involves specific fusagenic agents such as viral proteins, viral spike glycoproteins and peptides of viral spike glycoproteins. Vesicular stomatitis virus (VSV) fusion, for example, is thought to involve interaction between the VSV glycoprotein (G protein) and membrane lipids (Schlegel, R. et al. (1983) Cell 32:639–646). The VSV G protein reportedly binds preferentially to saturable receptors such as acidic phospholipid phosphatidylserine (Schlegel, R. and M. Wade (1985) J. Virol. 53(1):319–323). Fusion of influenza virus involves hemagglutinin HA-2N-terminal fusagenic peptides. See Kamata, H. et al. (1994) Nucl. Acids Res. 22(3):536–537.

Cell binding can also be enhanced or accelerated with peptides that bind cell receptors. For example, the pentonbase protein of the Adenovirus coat contains the peptide motif RGD (Arg-Gly-Asp) which mediates binding to integrins and vira internalization via receptor-mediated endocytosis (Wickham, T. J. et al. (1995) Gene Therapy 2:750–756).

The efficiency of cationic lipid transfections has recently been shown to be enhanced by the addition of whole virus particles to the transfection mixture. See Yoshimura et al. (1993) J. Biol. Chem. 268:2300. Certain viral components may also enhance the efficiency of cationic lipid-mediated transfection. See: U.S. patent applications Ser. Nos. 08/090, 290, filed Jul. 12, 1993, and 08/274,397, filed Jul. 12, 1994, incorporated by reference in their entirety herein. The use of peptides from viral proteins to enhance lipid-mediated transfections was also recently suggested by Kamata et al. (1994) Nucl. Acids Res. 22:536. Kamata et al. suggest that "LIPOFECTIN"-mediated transfections may be enhanced 3-4-fold by adding influenza virus hemagglutinin peptides to the transfection mixture. Despite these positive early indications, results vary as to the effectiveness of including fusagenic peptides in lipidic transfection compositions. Remy et al. (1995) Proc. Natl. Acad. Sci. U.S.A. 92:1744 report that "[a]ddition of lipids bearing a fusagenic or a nuclear localization peptide head group to the (polycationic lipid-DNA complex) particles does not significantly improve an already efficient system."

The present invention is based on the discovery that peptide sequences from viral proteins can significantly enhance the efficiency of cationic lipid-mediated transfection of eukaryotic cells. The compositions and methods of the invention comprise fusagenic receptor-ligand, or nuclear localization peptides which significantly improve the efficiency of transfection when bound to nucleic acid prior to adding the transfection reagent. These fusagenic, receptor-ligand, and nuclear localization peptides form a noncovalent association or complex with the DNA. Complex formation may be enhanced by covalently coupling the peptide to a DNA binding group, which binds to the nucleic acid through conformational or charge interactions between the binding group and the DNA. These bound nucleic acids are more efficiently transported into the cell and to the cell nucleus, thus requiring less nucleic acid starting material. The cationic lipid compositions of the present invention provide significant advantages over prior art compositions, including enhanced transformation frequency.

SUMMARY OF THE INVENTION

The present invention provides compositions and methods for transfecting eukaryotic cells, particularly higher eukaryotic cells, with nucleic acids. Nucleic acids, both DNA and RNA, are introduced into cells such that they retain their biological function. A composition for transfecting eukaryotic cells comprising a peptide-nucleic acid complex and a cationic lipid is provided. Transfecting compositions comprise a peptide or modified peptide which binds nucleic acid and which is fusagenic, or functions for nuclear localization or as a receptor-ligand. Receptor-ligand peptides include those that bind to cell surface receptors or cytosolic receptors that function for cell targeting or cell adhesion, and include those that trigger internalization or endocytosis. The peptide-nucleic acid complex is formed by interacting a peptide or modified peptide with nucleic acid. Modified peptides include peptides covalently conjugated to DNA-binding groups. The peptide-nucleic acid complex is subsequently combined with cationic lipid to form a peptide-nucleic acid-lipid aggregate which facilitates introduction of the anionic nucleic acid through cell membranes, including the nuclear membrane. The term peptide is used broadly herein to include peptides, polypeptides and proteins.

Peptides useful in transfection compositions include protein (or polypeptides) or functional portions thereof that are fusagenic, function for nuclear localization, are receptor ligands, comprise cell-adhesive signals, cell-targeting signals, cell-internalization signals or endocytosis signals as well as peptides or functional portions thereof of viral fusagenic proteins, of viral nuclear localization signals, of receptor-ligands, of cell adhesion signals, of cell targeting signals or of internalization- or endocytosis- triggering signals. Peptides useful in this invention include naturally occurring peptides, and synthetic analogs or functional equivalents of naturally occurring peptides. Transfecting compositions comprising viral peptides of influenza virus, vesicular stomatitis virus and simian virus 40 are of particular interest. Transfecting compositions containing viral peptides (as well as proteins and polypeptides) modified so that they are covalently conjugated to DNA-binding groups, for example, spermine or related polyamines, are also useful in the methods of this invention.

Inclusion of a peptide- or modified peptide-nucleic acid complex in a cationic lipid transfection composition significantly enhances transfection (2-fold or more) of the nucleic acid compared to transfection of the nucleic acid mediated by the cationic lipid alone. Enhancement of transfection by peptides or modified peptides is pronounced in a wide variety of cell lines, including human primary cell lines.

Monovalent or preferably polyvalent cationic lipids are employed in transfecting compositions. Preferred polyvalent cationic lipids are lipospermines, specifically DOSPA (2,3-droleylocy-N-[2(sperminecarboxamido)ethyl]-N,N-dimethyl-1-propanaminium trifluoroacetate). Cationic lipids are optionally combined with non-cationic lipids, particularly neutral lipids, for example lipids such as DOPE (dioleoylphosphatidyl-ethanolamine). A cationic lipid composition composed of a 3:1 (w/w) mixture of DOSPA and DOPE is generally useful in transfecting compositions of this invention. Preferred transfection compositions are those which induce substantial transfection of a higher eukaryotic cell line.

The methods of the present invention involve contacting a eukaryotic cell with a transfecting composition comprising a fusagenic, nuclear-localization, or receptor-ligand peptide, optionally conjugated to a DNA-binding group, wherein said peptide or modified peptide is non-covalently associated with the nucleic acid. A peptide-nucleic acid complex is formed and then combined with a cationic lipid. Methods of this invention employ among others, a viral peptide of influenza virus, vesicular stomatitis virus or simian virus 40. Methods of this invention are applicable to transfection of adherent or suspension cell lines, in general to animal cell lines, specifically to mammalian, avian, reptilian, amphibian and insect cell lines and more specifically to animal primary cell lines, human primary cell lines, stem cell lines, and fibroblasts.

In one specific embodiment, a fusagenic peptide is first bound to a nucleic acid to be introduced into a cell. The peptide-nucleic acid complexes are then admixed with cationic lipid and the resulting mixture is employed to transfect cells.

Preferred cationic lipid is a cationic lipid composition, more preferably of a polycationic lipid composition, and most preferably it is "LIPOFECTAMINE".

In a second specific transfection method, a fusagenic peptide or a receptor-ligand peptide is conjugated to a DNA-binding group to produce a modified peptide which is then bound to the nucleic acid to be introduced into the cell. The modified peptide-nucleic acid complexes are then admixed with cationic lipid and the resulting mixture is employed to transfect cells. In particular, the peptide is covalently conjugated to spermine, the spermine-modified peptide is complexed with nucleic acid and admixed with a cationic lipid. Preferentially, the cationic lipid is a cationic lipid composition, more preferably, it is a polycationic lipid composition and most preferably, it is "LIPOFECTAMINE".

In a third specific embodiment, a mixture of one or more fusagenic peptides, receptor-ligand peptides or nuclear localization peptides is mixed with and complexed with nucleic acid to be introduced into a cell. The peptide-nucleic acid complexes are then admixed with cationic lipid and the resulting mixture is employed to transfect cells.

The transfection methods of the present invention can be applied to in vitro and in vivo transfection of eukaryotic cells, particularly to transfection of higher eukaryotic cells including animal cells. The methods of this invention can be used to generate transfected cells which express useful gene products. The methods of this invention can also be employed as a step in the production of transgenic animals. The methods of this invention are useful as a step in any therapeutic method requiring introduction of nucleic acids into cells including methods of gene therapy and vital inhibition and for introduction of antisense or antigene or related inhibitory nucleic acids into cells. In particular, these methods are useful in cancer treatment, in in vivo and ex vivo gene therapy, and in diagnostic methods.

The transfection compositions of this invention comprising peptides, proteins, peptide fragments or modified-peptides, proteins or peptide fragments, can also be employed as research reagents in any transfection of eukaryotic cells done for research purposes. The transfection compositions can, with appropriate choice of physiologic medium, be employed in therapeutic and diagnostic applications.

Nucleic acids that can be transfected by the methods of this invention include DNA and RNA from any source comprising natural bases or non-natural bases, and include those encoding and capable of expressing therapeutic or otherwise useful proteins in cells, those which inhibit undesired expression of nucleic acids in cells, those which inhibit undesired enzymatic activity or activate desired enzymes, those which catalyze reactions (ribozymes), and those which function in diagnostic assays.

The compositions and methods provided herein can also be readily adapted in view of the disclosure herein to introduce biologically-active macromolecules other than nucleic acids including, among others, polyamines, polyamine acids, polypeptides and proteins into eukaryotic cells. Other materials useful, for example as therapeutic agents, diagnostic materials, research reagents, which can be bound to the peptides and modified peptides and introduced into eukaryotic cells by the methods of this invention.

DETAILED DESCRIPTION OF THE INVENTION

Figure 1:
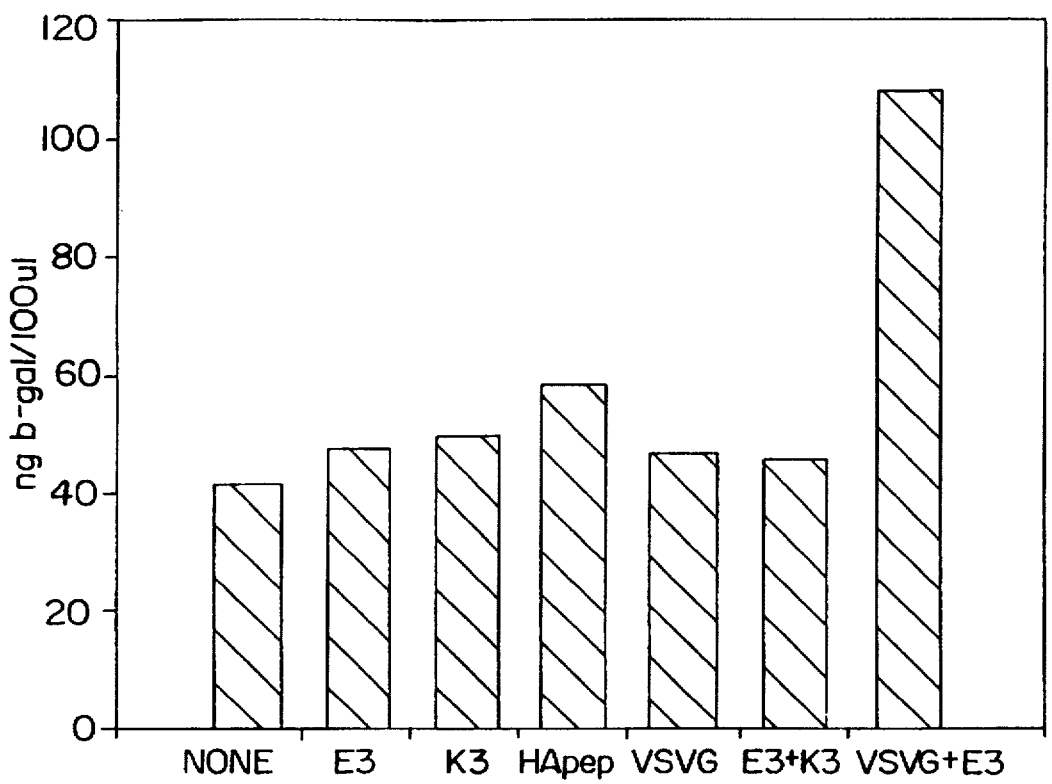
FIG. 1 is a bar graph showing enhancement of transfection of human fibroblast cells with various peptides added to "LIPOFECTAMINE"-DNA transfection mixtures.

The present invention provides improved methods for transfecting eukaryotic cells with nucleic acids by employing peptides or modified peptides and cationic lipids. The improvement relates to the use of a peptide-nucleic acid complex to enhance the efficiency of cationic lipid-mediated transfection. The peptide-nucleic acid complex comprises peptide bound to nucleic acid or a peptide modified to be covalently conjugated to a DNA-binding group which is then bound to nucleic acid. This invention has significant advantages over prior art methods of transfection which employ cationic lipids. The peptides of this invention include fusagenic peptides, nuclear localization peptides, and receptor-ligand peptides. Receptor-ligand peptides include among others cell-adhesion peptides, cell-targeting peptides, internalization-triggering peptides, and endocytosis-triggering peptides. Peptides useful in this invention may include peptide sequences functional for fusion (fusagenic sequences), nuclear localization or which mediate binding to a receptor. A peptide may be multi-functional comprising sequences with more than one of these functions. Peptides are optionally covalently coupled to a DNA-binding group including polyamine and form a complex with the nucleic acid. Peptide-complexed nucleic acids are more efficiently transported into the cells and the cell nucleus, thus enhancing the efficiency of cationic lipid-mediated cell transfection. Because of the improved efficiency of transfection, considerably less nucleic acid is required for effective transfection. The transfection compositions of the invention, by virtue of complex formation between the nucleic acid and peptide or modified peptide, provide enhanced transfection as compared to prior art cationic lipid transfection compositions.

The following definitions are employed in the specification and claims.

The term "transfection" is used herein generally to mean the delivery and introduction of biologically functional nucleic acid into a cell, e.g., a eukaryotic cell, in such a way that the nucleic acid retains its function within the cell. Transfection methods of this invention may be applied to cells in vitro or in vivo. The term transfection includes the more specific meaning of delivery and introduction of expressible nucleic acid into a cell such that the cell is rendered capable of expressing that nucleic acid. The term expression means any manifestation of the functional presence of the nucleic acid within a cell, including both transient expression and stable expression. Nucleic acids include both DNA and RNA without size limits from any source comprising natural and non-natural bases. Nucleic acids can have a variety of biological functions. They may encode proteins, comprise regulatory regions, function as inhibitors of gene or RNA expression (e.g., antisense DNA or RNA), function as inhibitors of proteins, function to inhibit cell growth or kill cells, catalyze reactions or function in a diagnostic or other analytical assay.

Transfection efficiency is "enhanced" when an improvement of at least about 5 percent, preferably about 10 percent, and more preferably about 20 percent in efficiency is shown using the protocols for measuring nucleic acid biological function set forth in the examples hereof. Transfection is substantially enhanced when at least about a 2-fold (i.e. 100% or more) improvement of efficiency is measured as described herein.

The term "DNA-binding group" is used herein generally to mean a protein, peptide, polypeptide or polyamine which is capable of non-covalently associating with nucleic acids. Binding of the DNA-binding group to the nucleic acid can be specific to the sequence of the nucleic acid, or non-specific to its sequence. Although the mechanism of association depends upon the particular binding group, sequence specificity generally results from an ensemble of mutually favorable interactions between a binding group and its target DNA. Some DNA-binding groups, for example, interact with the DNA's paired bases and sugar-phosphate chains through direct contacts, including hydrogen bonds, salt bridges and van der Waals forces. Other groups function through sequence-specific conformational variations in DNA rather than from sequence-specific hydrogen bonding interactions between DNA and protein. It will be understood that the term "DNA-binding group" includes any protein, peptide, polypeptide or polyamine which is capable of binding nucleic acid, without regard to the mechanism of binding. DNA-binding groups are known to the art and widely available in commerce.

The term "peptide" as used herein is intended to be a generic term which broadly includes short peptides (typically less than 100 amino acids), polypeptides (typically more than 100 amino acids, and proteins (which contain one or more polypeptide chains). The peptides of this invention typically have more than two amino acids; preferred peptides have more than 4 amino acids.

The peptides of this invention have biological function as fusagenic peptides (or proteins), nuclear-localization peptides (or proteins), and receptor-ligand peptides (or proteins).

Receptor-ligand peptides of this invention include those proteins or peptides which bind to cell-surface membrane or soluble receptor molecules and which optionally have another biological function and which optionally trigger internalization or endocytosis. Receptor-ligand peptides include cell-adhesion peptides (and proteins), and cell targeting peptides (and proteins).

Receptor-ligand peptides include adhesive peptides. Adhesive peptides do not typically trigger endocytosis. Adhesive proteins include fibronectin, vitronectin, tenascin, laminins, collagens, thrombospondins, fibrinogens and functional equivalent. Table 1 provides examples of adhesion proteins and peptides.

TABLE 1

Examples of Cell Adhesion Proteins

| LIGAND | BINDING REGION | REFERENCE |
|---|---|---|
| Fibronectin | RGD cell binding region (RGDSPC) (SEQ ID NO:11) - (all motifs) | Pierschbacher & Ruoslahti (1987) J. Biol. Chem. 262, 17294–17298 |
| Fibronectin 1 | including all cell binding regions RGD cell binding region (all motifs) | Pierschbacher & Ruoslahti (1984) Nature 209, 30–33 |
| Fibronectin 2 | RGD cell binding region (REDV/RGDV) (SEQ ID NOS:12/13) | Humphries et al., (1986) J. Cell Biol. 103, 2637–2647 |
| Fibronectin 3 | CS1 Fragment[1] | Humphries et al., (1987) J. Biol. Chem. 262, 6886–6892 |
| Vitronectin | RGD cell binding region (RGDV) (SEQ ID NO:13) | Suzuki et al., (1985) EMBO J. 4, 2519–2524 |
| Laminin 3 | RGD cell binding region (RGDN) (SEQ ID NO:14) | Grant et al., (1989) Cell 58, 933–943 |
| Tenascin 1 | RGD cell binding region (RGDM) (SEQ ID NO:15) | Friedlander et al., (1988) J. Cell Biol. 107, 2329–2340 |
| Collagen 1 | RGD cell binding region (RGDT) (SEQ ID NO:16) | Dedhar et al., (1988) J. Cell Biol. 104, 585–593 |
| Collagen 6 | RGD cell binding region (RGDX*) (SEQ ID NO:17) | Aumailley et al., (1989) Cell Res. 181, 463–474 |
| von Willebrand Factor | RGD cell binding region (RGDS) (SEQ ID NO:18) | Haverstack et al, (1985) Blood 66, 946–952 |
| Fibrinogen 1 | RGD cell binding region (RGDS) (SEQ ID NO:18) | Gardner and Hynes et al., (1985) Cell 42, 439–448 |
| Thrombospondin 1 | RGD cell binding region (RGDA) (SEQ ID NO:19) | Lawler et al., (1988) J. Cell Biol. 107, 2351–2362 |

[1]CS1 peptide sequence: DELPQLVTLPHPNLHGPEILDVPST (SEQ ID NO:20)
*X = various amino acids.

Fragments of adhesive proteins include RGD-containing peptides (RGD peptides) as listed in Table 1. The CS-1 peptide, sequence given in Table 1, is obtained from a 38 kD tryptic fragment of plasma fibronectin containing the carboxyl-terminal Heparin II domain and part of the type III connecting segment (IIICS) (Wayner, E. A. et al. (1989) "Identification and Characterization of T Lymphocyte Adhesion Receptor for an Alternative Cell Attachment Domain (CS-1) in Plasma Fibronectin" J. Cell Biol. 109:1321–1330.)

Receptor ligand peptides also include those that trigger internalization and/or endocytosis. For example, Penton Base is a pentamer coat protein of adenovirus that contains five copies of the integrin receptor binding motif, Arg-Gly-Asp (RGD). Penton Base is used by the virus to bind integrins $\alpha_v\beta_3$ and $\alpha_v\beta_5$. Following adenovirus attachment to cells by the fiber coat protein, the integrin receptors mediate virus internalization in to the host cells. The Penton Base (wild-type) RGD sequence is HAIRGGTFAT (SEQ ID NO:21) (Wickham, T. J. et al. (1995) Gene Therapy 2:750–756.)

Adhesive peptides include RGD peptides which are peptides containing the tripeptide sequence Arg-Gly-Asp which can duplicate or inhibit the cell attachment promoting effects of fibronectin or vitronectin (Pierschbacher, M. D., and Ruoslahti, E. (1987), J. of Biol. Chem. 262:17294–8), or other peptides with similar binding motifs.

Receptor-ligand peptides of this invention include those peptides that have an affinity for or binding to, receptor molecules that are broadly expressed in a variety of cell types, such as those peptides that bind to integrin $\alpha_v\beta_5$. Receptor-ligand peptides of this invention also include those peptides that bind to receptor molecules that are specifically expressed in a limited number of cell types (e.g. tissue-specific) or highly expressed in a particular cell type (e.g., in cancer cells, such as those that bind to the integrin $\alpha_v\beta_5$, which is highly expressed in certain melanomas and glioblastoma).

The term "modified-peptide" is used herein generally to mean a peptide (polypeptide or protein) which has been chemically modified to include a DNA-binding group covalently attached thereto. The term "modified-peptide" as used herein includes "polyamine-peptide conjugate" wherein the covalently attached DNA-binding group is a polyamine, including "spermine-modified peptide" wherein the DNA-binding group is spermine. In some cases, a peptide may itself bind to nucleic acid; in other cases modification of the peptide is necessary for or enhances binding to nucleic acid. Naturally, occurring peptides or proteins may require additional modification to allow conjugation to spermine or other polyamines. For example, cysteines may be added to the C-terminals or N-terminals of peptides or introduced within a peptide to facilitate conjugation. Any peptide modification used to facilitate conjugation should preferably not substantially affect peptide binding or function.

The term "peptide-nucleic acid complex" generally refers to the noncovalent association between a peptide and a nucleic acid. The peptide of this complex may be a modified peptide as defined above. As used herein, a "peptide-nucleic acid complex" is formed prior to the addition of cationic lipid to the transfection composition.

"Lipid aggregate" is a generic term that includes liposomes of all types both unilamellar and multilamellar as well as vesicles, micelles and more amorphous aggregates. A cationic lipid aggregate is a lipid aggregate comprising sufficient cationic lipid, optionally in combination with non-cationic lipids, such that the lipid aggregate has a net positive charge. Cationic lipids and lipid aggregates are capable of aggregating the peptide-nucleic acid complexes of the invention.

The term cationic lipid composition includes those compositions comprising a cationic lipid or a mixture of cationic lipids, which can be either monovalent or polyvalent cationic lipids. The cationic lipid composition optionally contains neutral lipids. Of particular interest are cationic lipid compositions recognized in the art as useful in transfection methods. Preferred cationic lipid compositions comprise polyvalent cationic lipids; more preferred are those compositions containing DOSPA and its analogs or homologs; the most preferred cationic composition is "LIPOFECTAMINE".

Transfection activity or efficiency is measured by detecting the presence of the transfected nucleic acid in a cell. This is often assessed by measuring the biological function of the nucleic acid in the cell, and most often assessed by measuring the level of transient or stable expression of a reporter gene comprised in the transfected nucleic acid. Reporter gene expression depends among other things on the amount of nucleic acid transfected as well as promoter function in the cell. Transfection activity can also be assessed by determining the percent of cells in a sample that have been transfected, for example, by assessing reporter gene expression using cell counting or in situ staining methods. The transfection methods of this invention employing peptides in combination with cationic lipids can display significant enhancement of transfection (2-fold or more) over transfection methods employing comparable cationic lipids alone.

The method of this invention involves contacting a eukaryotic cell with a transfection composition comprising a peptide-nucleic acid complex (or a modified peptide-nucleic acid complex) and a cationic lipid. The transfection composition optionally comprises a non-cationic lipid, preferably a neutral lipid. The peptide can be a fusagenic peptide of a viral protein. A preferred fusagenic peptide is that of influenza virus or vesicular stomatitis virus. The peptide can be a nuclear localization signal peptide. A preferred nuclear localization signal peptide is that of simian virus 40, particularly the nuclear localization sequence of the SV40 large T antigen. Kalderon et al. (1984) Cell 39:499; and Lanford et al. (1986) Cell 46:575. The peptide of this invention can be a receptor-ligand peptide. Preferred receptor-ligand peptides are cell adhesion peptides, particularly RGD peptides. Transfecting compositions comprising peptides of viral proteins conjugated to a DNA-binding group are particularly preferred. Preferred DNA-binding groups are polyamines, particularly spermine.

Enhanced transfection methods of this invention have been demonstrated with the prototype nuclear localization signal peptide from simian virus 40 and the prototype fusagenic peptides from influenza (HApep; E5 and K5 amphiphilic peptides), vesicular stomatitis virus (G protein) and an RGD peptide (GRGDSPC) (SEQ ID NO:10) taken from the cell attachment site of fibronectin. The DNA-binding group that has been employed is a polyamine capable of forming a noncovalent association with the base pairs of the nucleic acid. Enhanced transfection methods of this invention have been further exemplified using the prototype DNA-binding group, spermine.

In some cases, the peptides form a direct noncovalent association or complex with the nucleic acid. This peptide-nucleic acid complex forms as a consequence of conformational or charge interactions between the peptide and the base pairs of the DNA. A peptide-nucleic acid complex forms spontaneously in an appropriate medium. Transfection compositions comprising these peptide-nucleic acid complexes are prepared by first interacting the nucleic acid with the peptide followed by addition of the resulting complex to a cationic lipid composition.

The peptides of this invention, when covalently coupled to a DNA-binding group (modified-peptide), can form a noncovalent association or complex with the nucleic acid. This modified-peptide-nucleic acid complex forms as a consequence of conformational or charge interactions between the DNA-binding group and the DNA. For example, the prototype spermine-peptide-nucleic acid complex likely forms as a consequence of charge interactions between the amines of spermine and the phosphates on the DNA backbone. A modified-peptide-nucleic acid complex forms spontaneously in an appropriate medium. Transfection compositions comprising these modified-peptide-nucleic acid complexes are prepared by first interacting the nucleic acid with the modified peptide to form complexes followed by addition of a cationic lipid composition.

The transfection solution containing the peptide-nucleic acid or modified-peptide-nucleic acid complexes is then admixed with a cationic lipid, alone or in combination with a non-cationic lipid, to form a peptide-nucleic acid-lipid aggregate. A peptide-nucleic acid-lipid aggregate forms spontaneously in an appropriate medium or various well-known techniques may also be employed to produce a desired type of lipid aggregate. The relative amounts of cationic lipid and non-cationic lipid employed depends on a number of factors, including the toxicity of the lipids to the cell and the environment (e.g. medium) in which the aggregate is to be employed. The kinds and amounts of lipids employed is typically balanced to minimize cell toxicity and maximize transfection efficiency.

Nucleic acid delivery can be enhanced by the use of cell targeting, cell adhesive or binding peptides. Peptides containing the RGD sequence were coupled to the polycation spermine which acts as a DNA binding group.

The RGD-spermine peptide is believed to enhance transfection via cell targeting, and more importantly, cell adhesion. Attachment to adhesive proteins, and in some cases to other cells, is often mediated by integrins. Many adhesive proteins present in extracellular matrices and in the blood contain the tripeptide argenine-glycine-aspartic acid (RGD), as their cell recognition site (Ruoslahti, E. and Pierschbacher, D. (1987) Science 238:491). Pathogens such as bacteria, and more specifically, foot and mouth disease virus (FMDV) (Mason et al. (1994), Proc. Natl. Acad. Sci. 91, 1932–1936) and Adenovirus (Wickham, T. J. et al (1995), "Targeting of adenovirus penton base to new receptors through replacement of its RGD motif with other receptor-specific peptide motifs," in *Gene Therapy* 2:750–756) have RGD containing proteins expressed on their surface, which interact with integrins on the host cell and facilitate internalization. RGD and RGD-spermine peptide enhances "LIPOFECTAMINE"-mediated transfection.

Viral peptides can be isolated by a variety of well-known techniques, for example using the cationic detergent DTAB as described in Glushakova, S. E., et al. (1985) "Influenza viral glycoproteins isolation using cationic detergent dodecylmethylammonium bromide and its subsequent internalization into liposomal membrane" Mol. Genet. Microbiol. Virol. 4:39–44. Alternatively, viral peptides can be produced by a variety of standard chemical syntheses methods. Viral fusagenic peptides, for example, can be synthesized using automated solid phase peptide synthesis as described, e.g., in Stewart et al. (1984) *Solid Phase Peptide Synthesis*, Pierce Chemical Company, Rockford, Ill. Fusagenic peptides from influenza and vesicular stomatitis virus, including the exemplified hemagglutinin peptide, K5 and E5 amphiphilic peptides and G protein, are particularly useful in the methods of this invention. Nuclear localization signal peptides from simian virus 40, including the exemplified NLS peptide, are also preferred.

Modified-peptides can be prepared by a variety of well-known coupling techniques, for example using a heterobifunctional cross-linking agent as described in the Examples hereof. A variety of cross-linking agents are known to the art and widely available in commerce including, without limitation, succinimidyl or maleimidyl cross-linkers, such as Sulfosuccinimidyl 4-(p-maleimidophenyl)butyrate (Sulfo-SMPB), disuccinimidyl suberate, succinimidyl 4-(p-maleimidophenyl)butyrate (SMPB), 4-succinimidyloxycarbonyl-α-methyl-α-(2-pyridyldithio)-toluene (SMPT), Sulfosuccinimidyl 6-[3-(2-pyridyldithio) propionamido]hexanoate (Sulfo-LC-SPDP), Succinimidyl 6-[3-(2-pyridyldithio)propionamido]hexanoate (LC-SPDP), N-Succinimidyl 3-(2-pyridyldithio)propionate (SPDP), Sulfosuccinimidyl 4-(N-maleimidomethyl)cyclohexane-1-carboxylate (Sulfo-SMCC), Succinimidyl 4-(N-maleimidomethyl)cyclohexane-1-carboxylate (SMCC); m-Maleimidobenzoyl-N-hydroxysulfosuccinimide ester (Sulfo-MBS), m-Maleimidobenzoyl-N-hydroxysuccinimide ester (MBS), Sulfosuccinimidyl(4-iodoacetyl) aminobenzoate (Sulfo-SIAB), N-Succinimidyl (4-iodoacetyl)aminobenzoate (SIAB). Methods for conjugating peptides and polyamines are well-known in the art. Representative methods are disclosed in Staros, J. V. (1982) Biochemistry 21:3990.

Media employed in transfections should preferably be free of components, like serum or high salt levels, that can inhibit cationic lipid-mediated transfection of cells.

A variety of cationic lipids is known in the art. Generally, any cationic lipid, either monovalent or polyvalent, can be used in the compositions and methods of this invention. Polyvalent cationic lipids are generally preferred. Cationic lipids include saturated and unsaturated alkyl and alicyclic ethers and esters of amines, amides or derivatives thereof. Straight-chain and branched alkyl and alkene groups of cationic lipids can contain from 1 to about 25 carbon atoms. Preferred straight-chain or branched alkyl or alkene groups have six or more carbon atoms. Alicyclic groups can contain from about 6 to 30 carbon atoms. Preferred alicyclic groups include cholesterol and other steroid groups. Cationic lipids can be prepared with a variety of counterions (anions) including among others: Cl$^-$, Br$^-$, I$^-$, F$^-$, acetate, trifluoroacetate, sulfate, nitrite, and nitrate.

A well-known cationic lipid is N-[1-(2,3-dioleoyloxy)-propyl]-N,N,N-trimethylammonium chloride (DOTMA). See Felgner, P. L. et al. (1987) Proc. Natl. Acad. Sci. U.S.A. 84:7413–7417. DOTMA and the analogous diester DOTAP (1,2-bis(oleoyloxy)-3-3-(trimethylammonium)propane) are commercially available. Additional cationic lipids structurally related to DOTMA are described in U.S. Pat. No. 4,897,355, which is incorporated by reference in its entirety herein.

Other useful groups of cationic lipids related to DOTMA and DOTAP are commonly called DORI-ethers or DORI-esters. DORI lipids differ from DOTMA and DOTAP in that one of the methyl groups of the trimethylammonium group is replaced with a hydroxyethyl group. The DORI lipids are similar to the Rosenthal inhibitor (RI) of phospholipase A (Rosenthal, A. F. and Geyer, R. P. (1960) J. Biol. Chem. 235:2202–2206). The oleoyl groups of DORI lipids can be replaced with other alkyl or alkene groups, such as palmitoyl or stearoyl groups. The hydroxyl group of the DORI-type lipids can be used as a site for further functionalization, for example for esterification to amines, like carboxyspermine.

Additional cationic lipids which can be employed in the compositions and methods of this invention include those described as useful for transfection of cells in PCT application WO 91/15501 published Oct. 17, 1991, Pinnaduwage, P. et al. (1989) Biochem. Biophys. Acta. 985:33–37; Rose, J. K. et al. (1991) BioTechniques 10:520–525; Ito, A et al. (1990) Biochem, Intern. 22:235–241.

The polycationic lipid formed by conjugating polylysine to DOPE (Zhou, X. et al. (1991) Biochem. Biophys. Acta 1065:8–14), as well as other lipopolylysines, can also be employed in the methods and compositions of this invention.

Polycationic lipids containing carboxyspermine are also useful in the compositions and methods of this invention. Behr, J. -P. et al. (1989) Proc. Natl. Acad. Sci. 86:6982–6986 and EPO published application 304 111 (1990) describe carboxyspermine-containing cationic lipids including 5-carboxyspermylglycine dioctadecyl-amide (DOGS) and dipalmitoylphosphatidylethanolamine 5-carboxyspermylamide (DPPES). Additional cationic lipids can be obtained by replacing the octadecyl and palmitoyl groups of DOGS and DPPES, respectively, with other alkyl or alkene groups.

U.S. Pat. No. 5,334,761, which is incorporated by reference in its entirety herein, also describes cationic lipids which are useful in this invention.

In the transfection compositions of this invention cationic lipids can optionally be combined with non-cationic lipids, preferably neutral lipids, to form lipid aggregates that bind to the modified-peptide-nucleic acid complex. Neutral lipids useful in this invention include, among many others: lecithins; phosphotidyletahnolamine; phosphatidylethanolamines, such as DOPE (dioleoylphosphatidyl-ethanolamine), POPE (palmitoyloleoyl-phosphatidylethanolamine) and distearoylphosphatidylethanolamine; phosphotidylcholine; phosphatidylcholines, such as DOPC (dioleoylphosphidylcholine), DPPC (dipalmitoylphosphatidylcholine) POPC (palmitoyloleoyl-phosphatidylcholine) and distearoylphosphatidylcholine; phosphatidylglycerol; phosphatidylglycerols, such as DOPG (dioleoylphosphatidylglycerol), DPPG (dipalmitoylphosphatidyl-glycerol), and distearoylphosphatidylglycerol; phosphatidyl-serine; phosphatidylserines, such as dioleoyl- or dipalmitoylphospatidylserine; diphosphatidylglycerols; fatty acid esters; glycerol esters; sphingolipids; cardolipin; cerebrosides; and ceramides; and mixtures thereof. Neutral lipids also include cholesterol and other 3βOH-sterols.

The present invention is based on the discovery that certain peptides or modified peptides can significantly enhance the efficiency of transfection of eukaryotic cells with nucleic acids. The peptide or modified peptide binds to the DNA and functions as a fusagenic peptide, functions for nuclear localization or for cell adhesion. Peptides, optionally modified, if necessary or desirable, to enhance binding to nucleic acids, that function as internalization-triggering signals or endocytosis-triggering signals, also function in the transfection methods of this invention. The compositions and methods of the invention comprise peptides, optionally modified covalently with a DNA-binding group, which significantly improve the efficiency of transfection when bound to nucleic acid prior to adding the transfection reagent. These bound nucleic acids are more efficiently transported into the cell and to the cell nucleus, thus requiring less nucleic acid starting material. Although the present invention is exemplified using a cationic lipid delivery system, fusagenic and nuclear localization peptides are effective in enhancing transfection using a variety of known delivery systems. The present invention thus contemplates the use of these peptides to enhance transfection using other delivery means including, without limitation, electroporation (T. K. Wong and E. Neumann (1982) *Biochem. Biophys. Res. Commun.* 107:584 and E. Neumann et al. (1982) *EMBO J.* 1:841), calcium phosphate (F. L. Graham and A. J. Vander Eb (1973) *Virology* 52:456), microinjection (M. R. Capecchi (1920) 22:479), ballistic transformation using microscopic particles coated with DNA (D. T. Tomes et al. (1990) *Plant Mol. Biol. Manual* A13:1–22 and G. N. Ye et al. (1990) *Plant. Molec. Biol.* 15:809) DEAE-dextran (A. Vaheri and J. S. Pagano (1965) *Science* 175:434), and polybrene-DMSO (S. Kawai and M. Nishizawa (1984) *Molec. Cell. Biol.* 4:1172).

Transfection compositions of this invention include compositions for transfecting eukaryotic cells using a peptide or protein comprising a nuclear localization sequence, a fusagenic peptide or receptor-ligand peptide sequence crosslinked to a polycation. Peptides having a nuclear localization sequence, fusagenic peptide or receptor-ligand signal crosslinked to a polycation, are also a part of the invention. Preferred crosslinkers include, for example, heterobifunctional crosslinkers. The polycation is preferably a polyamine and most preferable, spermine. As previously discussed, the transfection compositions and peptides of the invention are useful with a wide variety of delivery systems including, without limitation, electroporation, calcium phosphate, microinjection, ballistic transformation, DEAE-dextran and polybrene-DMSO. The present invention thus includes methods for transfecting a eukaryotic cell with a nucleic acid, the method generally comprising the steps of (1) admixing a peptide or modified peptide with a nucleic acid to form a peptide-nucleic acid complex; and (2) introducing the peptide-nucleic acid complex from step (1) into the cell using a known delivery means. One of ordinary skill in the art, based on knowledge generally available to the art including the present disclosure, can use the compositions and peptides of the present invention with any delivery system without the expense of undue experimentation.

It will be readily apparent to those of ordinary skill in the art that a number of parameters are important for optimal transfection. These parameters include cationic lipid concentration, relative amounts of cationic and non-cationic lipid, the concentration of nucleic acid, the medium employed for transfection, the length of time the cells are incubated with transfection composition, the amount of peptide employed, the amount of DNA-binding group or polyamine employed, and the way in which the components of the transfection composition are combined. It may be necessary to optimize these parameters for each cell type to be transfected. Such optimization is routine employing the guidance provided herein and transfection assays as described in the Examples herein.

It will also be apparent to those of ordinary skill in the art that alternative methods, reagents, procedures and techniques other than those specifically detailed herein can be employed or readily adapted to produce the transfection compositions of this invention and practice the transfection methods of this invention. Such alternative methods, reagents, procedures and techniques are within the spirit and scope of this invention.

The transfection compositions and methods of this invention are further illustrated in the following non-limiting Examples. All abbreviations used herein are standard abbreviations in the art. Specific procedures not described in detail in the Examples are well-known in the art.

All publications and patents referred to herein are specifically incorporated by reference in their entirety.

EXAMPLES

Example 1

Cell Cultures and Plasmids

Human primary fibroblasts (HPF) were isolated from neonatal foreskin dermis and prepared as described in Hawley-Nelson, P., et al. (1993) *Focus* 15:73, incorporated by reference herein, and cultured for up to 20 passages. HT1080 (human fibrosarcoma cells), CHO-K1 (Chinese hamster ovary), NIH/3T3 (NIH Swiss mouse embryo, contact-inhibited fibroblasts), K562 (human chronic myelogenous leukemia), Jurkat (Acute T-cell lymphoma, human) and baby hamster kidney (BHK-21) cells were obtained from the American Type Culture Collection (Rockville, Md.). Cultures of adherent cells were grown in Dulbecco's-modified Eagle's medium (DMEM) containing 10% (v/v) fetal bovine serum (FBS), 100 U/mL penicillin (PEN) and 100 mg/mL streptomycin (STREP). Cultures were passaged at confluence using 0.25% (v/v) trypsin, 0.1 mM EDTA. Cultures of suspension cells (Jurkat and K562) were grown as described in the following examples. All culture reagents were from Gibco/BRL (Life Technologies, Inc., Gaithersburg, Md.).

The plasmid vectors pCMVβgal and pCMVSPORTβgal are commercially available (Clontech, Calif. and G1B60-BRL, respectively) mammalian reporter vector containing the *E. coli* β-galactosidase (β-gal) gene under the control of the Cytomegalovirus promoter. See: MacGregor et al. (1989) *Nucleic Acids Res.* 17:2365; Norton et al. (1985) *Mol. and Cell Biol.* 5:281; Alam (1990) *Anal. Biochem.* 188:245. Plasmid DNA was purified by standard cesium chloride methods.

Example 2

Peptides and Peptide-Spermine Conjugates

Peptides were synthesized using automated solid phase peptide synthesis as described, e.g., in Stewart et al. (1984) *Solid Phase Peptide Synthesis*, Pierce Chemical Company, Rockford, Ill. Peptides were synthesized using a polyamide-kieselguhr composite resin and a MilliGen 9050 peptide synthesizer (MilliGen/Biosearch, Burlington, Mass.); coupling cycles were performed according to the manufacturer's recommendations including the following: 9-fluorenyl-methyloxy-carbonyl (Fmoc) amino acid is activated as pentafluorophenyl ester (-OPfp ester), deprotect alpha-amino groups by 20% piperidine in N,N-dimethylformamide (DMF), cleave peptide from resin and deprotect by 95% trifluoroacetic acid (TFA), precipitate and wash crude peptide with ether. Peptides were purified by high pressure liquid chromatography on a Vy-Dac C(18) reverse-phase column using a Waters system. The mobile phase consisted of a gradient from 0.01% TFA in 95% water/acetonitrile to 0.01% TFA in 25% water/acetonitrile. Peptide sequences are shown in Tables 1 and 2.

Peptide-spermine conjugates were prepared using a heterobifunctional cross-linking agent sulfo-SMPB (Pierce Chemical Co., Rockford, Ill.). Briefly, 100 mg/mL sulfo-SMPB in DMF was diluted to 20 mg/mL using 50 mM sodium phosphate buffer (pH 7.5). 50 mg/mL spermine in 50 mM sodium phosphate buffer was then added to the sulfo-SMPB solution at a 3:1 molar ratio. After 1 hour at room temperature, the reaction mixture was fractionated (LH-20 column) using the sodium phosphate buffer. The first major peak (spermine-MPB) was collected and mixed at a 1:1.5 to 1:2 ratio with synthetic peptide, either in pure powder form or in acetonitrile/water solution. Excess peptide was separated on a LH-20 column eluted with water. The peptide-spermine conjugate was stored frozen until use.

Example 3

Transfection of Human Primary Fibroblast and BHK-21 Cells

For transfection, cells were trypsinized the day prior to treatment and replated at $8 \times 10^4$ or $1 \times 10^5$ (human fibroblasts) or $2 \times 10^4$ (BHK-21) cells per well in 24-well plates. Cells were rinsed once with serum-free DMEM prior to transfection and 0.25 mL serum-free DMEM was added to each well. Plasmid DNA was diluted to 10 mg/mL in "OPTI-MEM"-I reduced serum medium (a modification of MEM (Eagle's) which contains HEPES buffer, 2,400 mg/L sodium bicarbonate, hypoxanthine, thymidine, sodium pyruvate, L-glutamine, trace elements and growth factors (Gibco/BRL: Life Technologies, Inc., Gaithersburg, Md.) medium and allowed to bind to or complex with various concentrations of enhancing peptides (7–470 μM) for 30 minutes at room temperature. "LIPOFECTAMINE" (Gibco/BRL: Life Technologies, Inc., Gaithersburg, Md.) was separately diluted in "OPTI-MEM"-I (40–400 μg/mL) and allowed to incubate for 5 minutes at room temperature. "LIPOFECTAMINE" is a 3:1 (w/w) mixture of the polycationic lipid, 2,3-dioleyloxy-N-[2(sperminecarboxamido)ethyl]-N,N-dimethyl-1-propanaminium trifluoroacetate (DOSPA), and DOPE. After this pre-incubation period, the diluted peptide-DNA complex mixture was gently mixed with an equal volume of the diluted transfection reagent. The reaction mixture was incubated at room temperature for 30 minutes to form peptide-DNA-lipid aggregates. The aggregates were then diluted 6-fold with serum-free DMEM and 0.3 mL diluted aggregate was added to each well. Cells were incubated at 37° C. After approximately 5 hours, one mL growth medium (DMEM containing 13% FBS) was added to each well. Cells were assayed the next day for β-galactosidase activity.

Example 4

Transient Transfection Assays

In situ staining was used to demonstrate β-galactosidase expression (Sanes, J. R. et al. (1986) EMBO J. 5:3133). Cells were rinsed with PBS, fixed for 5 min in 2% (v/v) formaldehyde, 0.2% glutaraldehyde in PBS, rinsed twice with PBS, and stained overnight with 0.1% X-gal (Gibco/BRL: Life Technologies, Inc., Gaithersburg, Md.), 5 mM potassium ferrocyanide, 5 mM potassium ferrocyanide, 2 mM $MgCl_2$ in PBS. Rinsed cells were photographed using a 10X objective on a Nikon inverted microscope with Hoffman optics. Transfection efficiency is evaluated by counting or estimating the number of β-gal positive (blue-stained) cells.

Enzyme activity of lysed cell extracts was used to compare levels of expression resulting from different treatment protocols. One to two days following transfection, cells were rinsed once with PBS and frozen at $-70°$ C. in 0.15–0.25 mL/well 0.1% "TRITON" X-100 (t-octylphenoxypolyethoxyethanol; Sigma Chemical Co., St. Louis, Mo.; "TRITON" is a trademark of Union Carbide, Inc.) and 0.1M Tris, pH 8.0. After rapid thawing at 37° C., the lysate was cleared by centrifugation. Lysed cell extracts were assayed for β-galactosidase activity employing the method essentially as described in Sambrook et al. (1989) Molecular Cloning A Laboratory Manual, $2^{nd}$ Ed., Cold Spring Harbor Laboratory Press, p. 16.66. Briefly, soluble cell extract containing 2–6 μg protein was added to 100 μl 0.1M sodium phosphate buffer (pH 7.5) containing 1 mM $MgCl_2$, 50 mM β-mercaptoethanol and 0.88 mg/mL o-nitrophenyl-β-D-galacatopyranoside (ONPG) in a 96-well microtiter plate. A standard curve of 10–70 ng β-galactosidase (Gibco/BRL: Life Technologies, Inc., Gaithersburg, Md.) was included on the plate. Yellow color developed in 5–20 minutes at 37° C. The reaction was stopped by adding 150 μl 1M $Na_3CO_2$; $OD_{420}$ was determined on a microtiter plate reader.

Example 5

Transfection of Human Fibroblast Cells using Cationic Lipids and Viral Peptides

The following vital peptides were synthesized using automated solid phase peptide synthesis as described in Example 2: the membrane fusion regions of influenza virus hemagglutinin, peptides E5 and K5 (see, Kamata, H. et al. (1994) Nucleic Acids Res. 22:536–537); hemagglutinin peptide, HApep (see, Epand et al. (1992) Biopolymers 32:309); vesicular stomatitis virus G-protein, VSVG (see, Schlegel, R. and Wade, M. (1985) J. Virol. 53:319); and the nuclear localization signal of SV40 large T antigen, NLS (see, Lanford et al. (1986) Cell 46:575). The RGD peptide of Examples 12 and 13 was also synthesized as in Example 2, (Ruoslahti, E. and Pierschbacher, D. (1987) Science 238:491).

Human fibroblasts were plated the day before transfection at $8 \times 10^4$ per well on a 24-well dish. Before transfection, the cells were rinsed with serum-free DMEM. Two 25 μl aliquots of "OPTI-MEM"-I medium, one containing 3 μg "LIPOFECTAMINE" and the other containing 0.2 μg pCMVβgal DNA, were combined to form complexes for 30 min at room temperature. Peptides were dissolved in dimethylsulfoxide (DMSO) at 250× the final concentration (see Table 1). 1 μl peptide solution was added to 250 μl serum-free DMEM transfection medium and added to the rinsed cells. Treatments containing the E5, K5, HApep, and VSVG alone, and E5+K5 and VSVG+K5 in combination with each other were compared to a transfection sample containing no peptide ("LIPOFECTAMINE"+DNA only). For treatments that combined two peptides, E5, K5 and VSVG were all used at 5 μM concentrations. The DNA-lipid aggregates in "OPTI-MEM"-I were then added to the transfection medium with added peptide(s) on the cells. After 24 hours incubation at 37° C., cells were harvested, extracted and assayed for β-galactosidase activity as described in Example 4.

As shown in FIG. 1, relatively minor enhancements of transfection compared to the control were observed except for HApep and the combination of VSVG and E5. The VSVG+E5 combination showed greater than 2-fold enhancement compared to "LIPOFECTAMINE" alone. Peptide concentrations that resulted in optimal transfection are listed in Table 2.

TABLE 2

Viral peptides tested for enhancement of "LIPOFECTAMINE" transfections.

| Peptide | Sequence | Concentration (μM) |
|---|---|---|
| E5 | GLFEAIAEFIEGGWEGLIEG (SEQ ID NO:1) | 0.1 |
| K5 | GLFKAIAKFIKGGWKGLIKG (SEQ ID NO:2) | 5 |
| HApep | GLFGAIAGFIENGWEGMIDG (SEQ ID NO:3) | 10 |
| VSVG | KFTIVF (SEQ ID NO:4) | 1 |
| NLS | GYGPKKKRKVGG (SEQ ID NO:5) | Not tested |
| RGD | GRGDSPC (SEQ ID NO:10) | Not tested |

Example 6

Transfection of Human Fibroblast Cells using Cationic Lipids and Spermine-Peptide Conjugates The NLS and VSVG peptides (Example 5) were synthesized with cysteine in the N- or C- terminal position, then conjugated to spermine as described in Example 2. These spermine-peptide conjugates were then evaluated to determine the effect of covalently bound spermine on the efficiency of transfection. Human fibroblasts were plated the day before transfection at $8 \times 10^4$ per well on a 24-well plate. Before transfection, the cells were rinsed with serum-free DMEM. Aqueous solutions of 0.15 mM spermine-modified peptides were prepared, each diluted to 50 μM concentrations using "OPTI-MEM"-I containing 6 μg/mL DNA, then incubated at room temperature. After 15 minutes, an equal volume of "OPTI-MEM"-I containing 120 μg/mL "LIPOFECTAMINE" was added, and the mixtures were incubated for 30 minutes to allow complex formation. These complexes in "OPTI-MEM"-I were diluted 6-fold with serum-free DMEM, and 0.3 mL of diluted complex was added to each well. After approximately 5 hours incubation at 37° C., one mL DMEM containing 10% (v/v) FBS was added to each well. The next day cells were fixed and stained with X-gal, as described in Example 4. The level of expression was estimated by observation and reported as fold enhancement of peak "LIPOFECTAMINE" transfection levels without peptide. The results are shown in Table 3. As shown in Table 3, covalent binding of spermine to NLS and VSVG peptides causes a significant enhancement in the efficiency of cationic lipid transfection.

TABLE 3

Spermine-modified peptide enhancement of "LIPOFECTAMINE" transfections

| Peptide | Sequence | Fold Enhancement |
|---|---|---|
| NLS-sp | GYGPKKKRKVGGCsp (SEQ ID NO:6) | 1–2 |
| Short NLS-sp | PKKKRKVGGCsp (SEQ ID NO:7) | 1 |
| sp-NLS | spCGYGPKKKRKVGG (SEQ ID NO:8) | 5–10 |
| VSVGsp | KFTIVFCsp (SEQ ID NO:9) | 3–5 |

Figure 2:
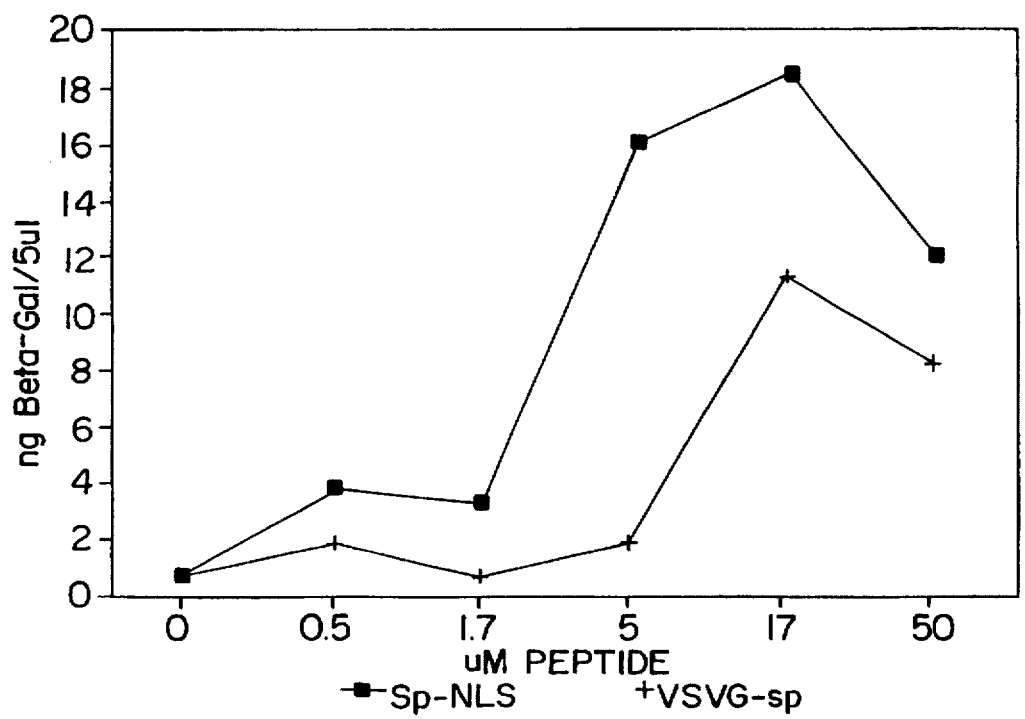
FIG. 2 is a graph showing enhancement of transfection of human fibroblasts by including varying concentrations of spermine-NLS and spermine-VSVG complexed to DNA prior to addition of "LIPOFECTAMINE".

The spermine-NLS and spermine-VSVG conjugates were further tested to determine the optimal concentration for enhancement. Human fibroblasts were plated the day before transfection at $8 \times 10^4$ per well on a 24-well dish. Before transfection, the cells were rinsed with serum-free DMEM. Two 25 mL aliquots of "OPTI-MEM"-I medium were prepared; one contained 3 μg "LIPOFECTAMINE" and the second contained 0.2 μg pCMVβgal DNA. Spermine-peptide conjugates were dissolved in water at 25-fold their final concentration. 10 μl spermine-peptide solution was added to the "OPTI-MEM"-DNA aliquot and incubated for 15 minutes at room temperature. The "LIPOFECTAMINE" solution was then added to the DNA-peptide solution, and the mixture incubated 30 minutes at room temperature to allow complex formation. The complex solution was diluted to 0.3 mL with serum-free DMEM and added to each well. After approximately 5 hours incubation at 37° C., one mL DMEM containing 10% (v/v) FBS was added to each well. The next day cells were harvested, lysed and lysed cell extracts were assayed for β-galactosidase activity, as described in Example 4. The results are shown in FIG. 2. As shown in FIG. 2, 5 to 17 μM final concentration of spermine-modified peptide in the transfection medium (5-10-fold higher concentration in the pre-incubation with DNA) was found to be optimal.

Example 7

Figure 3:
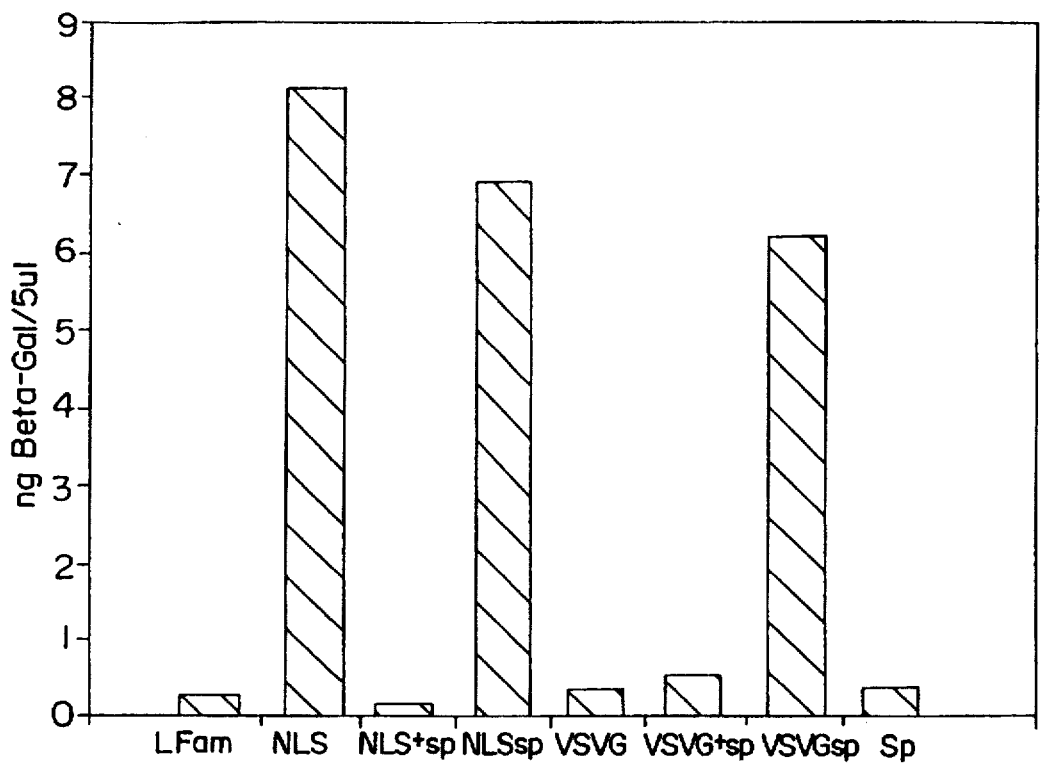
FIG. 3 is a bar graph showing enhancement of transfection of human fibroblasts by including a combination of DNA with spermine, mixtures of spermine and peptide-DNA complexes and various peptide-DNA complexes.

Comparison of Peptides, Spermine-Peptide Conjugates and Spermine/Peptide Mixtures Transfection of Human Primary Fibroblast Cells The NLS and VSVG peptides (Example 5) were synthesized with an additional cysteine in the N- or C- terminal position, then conjugated to spermine as described in Example 2. These spermine-peptide conjugates were then evaluated for enhancement of transfection relative to the corresponding spermine/peptide mixture. Human fibroblasts were plated the day before transfection at $8 \times 10^4$ per well on a 24-well dish. Before transfection, cells were rinsed with serum-free DMEM. Two 25 μl aliquots of "OPTI-MEM"-I medium were prepared, one containing 3 μg "LIPOFECTAMINE" and the second containing 0.2 μg pCMVβgal DNA. Spermine-peptide conjugates or mixtures of peptides with and without spermine were dissolved in water at 25-fold their final concentration. 10 μl peptide was added to the "OPTI-MEM"-DNA aliquot and incubated for 15 minutes at room temperature. The "LIPOFECTAMINE" solution was added to the DNA-peptide solution, and incubated 30 minutes at room temperature to allow complex formation. The complex solution was diluted to 0.3 mL with serum-free DMEM and added to each well. After approximately 5 hours incubation at 37° C., one mL DMEM containing 10% (v/v) FBS was added to each well. The next day cells were harvested, lysed and lysed cell extracts were assayed for β-galactosidase activity, as described in Example 4. The results as shown in FIG. 3. As shown in FIG. 3, the addition of spermine to the unconjugated peptides does not enhance transfection. Surprisingly, the addition of the NLS peptide without the terminal spermine residue, when allowed to complex with the DNA before addition of "LIPOFECTAMINE", enhanced transfection as much or more than the spermine-NLS conjugate.

Example 8

Effect of Order of Reagents on Transfection of Human Primary Fibroblast Cells

Figure 4:
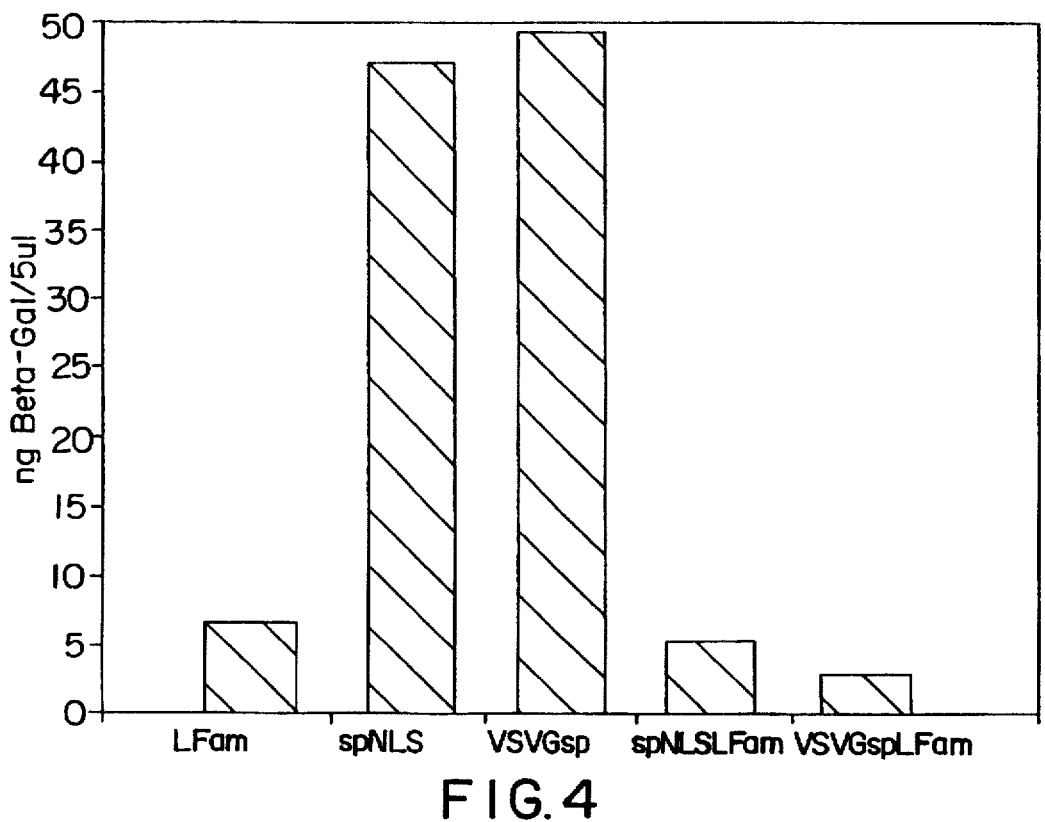
FIG. 4 is a bar graph showing the effect of order of addition of reagents on enhancement of transfection of human fibroblast cells.

The spermine-NLS and spermine-VSVG peptides were synthesized as described in Example 2. Transfection protocols were as described in Example 3, except that the order of addition of reagents was varied to test the effect on transfection of complex formation between the spermine-modified peptide and DNA. Results are shown in FIG. 4.

Human fibroblasts were plated the day before transfection at $8 \times 10^4$ per well on a 24-well dish. Before transfection, cells were rinsed with serum-free DMEM. Two 25 μl aliquots of "OPTI-MEM"-I medium were prepared, one containing 3 μg "LIPOFECTAMINE" and the other containing 0.2 μg pCMVβgal DNA. To form spermine-modified-peptide-DNA complexes, spermine-peptide conjugates were dissolved in water at 25-fold their final concentration, then 10 μl peptide solution was added to the "OPTI-MEM"-DNA aliquot and incubated for 15 minutes at room temperature. To test the effect of order of addition on reagents, the peptides were first added to the diluted "LIPOFECTAMINE" in "OPTI-MEM"-I and incubated 15 minutes at room temperature before mixing with the DNA solution. The "LIPOFECTAMINE"/peptide solution was then added to the DNA solution and incubated 30 minutes at room temperature to allow lipid-DNA complex formation. The complex solution was diluted to 0.3 mL with serum-free DMEM and added to each well. After approximately 5 hours incubation at 37° C., one mL DMEM containing 10% (v/v) FBS was added to each well. The next day cells were harvested, lysed and lysed cell extracts were assayed for β-galactosidase activity, as described in Example 4. The results are shown in FIG. 4. As shown in FIG. 4, the addition of the spermine-peptide conjugate to the transfection lipid prior to complexing with DNA significantly reduces the efficiency of transfection.

Example 9

Figure 5:
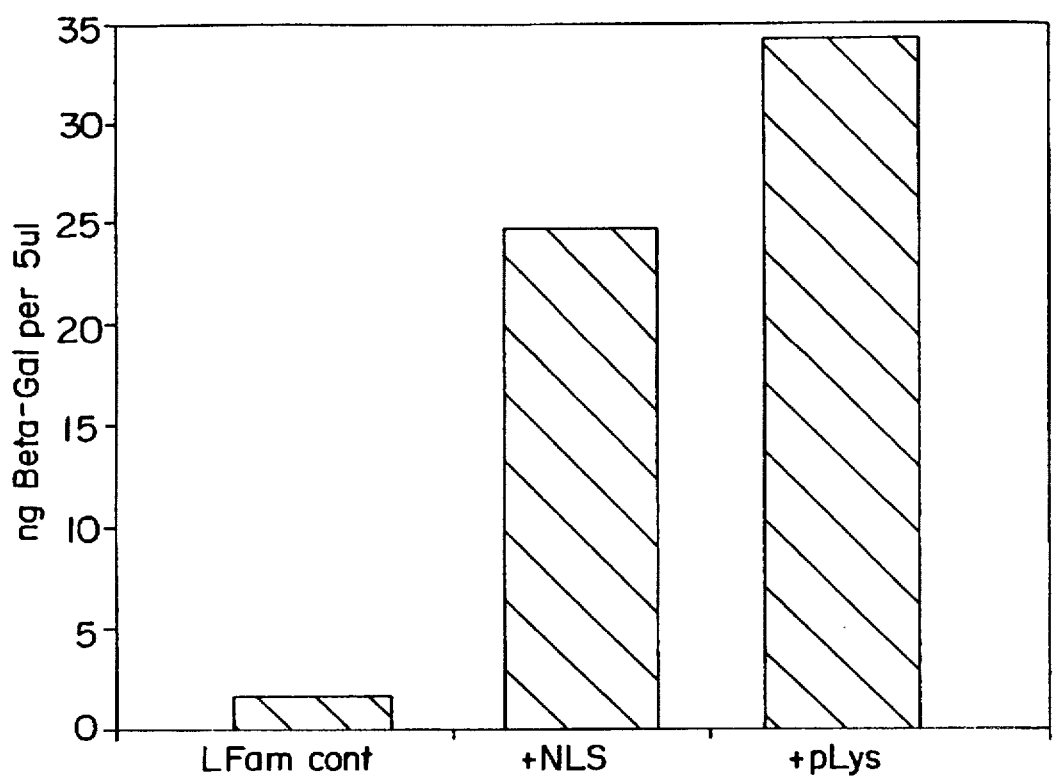
FIG. 5 is a bar graph showing enhancement of transfection of human fibroblasts by including NLS-DNA and poly-L-lysine-DNA complexes in "LIPOFECTAMINE".

Transfection of Human Primary Fibroblast Cells Using Spermine-Modified-Peptide or Poly-L-Lysine and Cationic Lipids The spermine-NLS peptide was synthesized as described in Example 2. Poly-L-lysine (MW 5200) was obtained from Sigma Chemical Co. (St. Louis, Mo.). Transfection protocols were as described in Example 3, except that poly-L-lysine was used to compare the effect of a poly-amino acid/DNA complex with the effect of the spermine-peptide-DNA complex on transfection. Human fibroblasts were plated the day before transfection at 8 ×10⁴ per well on a 24-well dish. Before transfection, cells were rinsed with serum-free DMEM. Two 25 μL aliquots of "OPTI-MEM"-I medium were prepared, one containing 3 μg "LIPOFECTAMINE" and the other containing 0.2 μg pCMVβgal DNA. Spermine-conjugated NLS and poly-L-lysine were dissolved in water at 25-fold their final concentration. 10 μL peptide was added to the OPTI-MEM-DNA aliquot and incubated for 15 minutes at room temperature. The "LIPOFECTAMINE" solution was added to the DNA-peptide solution, and incubated 30 minutes at room temperature to allow lipid-DNA-peptide complex formation. The complex solution was diluted to 0.3 mL with serum-free DMEM and added to each well. After approximately 5 hours incubation at 37° C., one mL DMEM containing 10% (v/v) FBS was added to each well. The next day cells were harvested, lysed and lysed cell extracts were assayed for β-galactosidase activity, as described in Example 4. The results as shown in FIG. 5. As shown in FIG. 5, complex formation of 0.1 mM poly-L-lysine (MW5200) with the DNA prior to formation of complexes with lipid transfection reagents enhanced transfection at least as much as the spermine-NLS precomplexed to the DNA.

Example 10

Transfection of BHK-21 Cells Using Spermine-NLS Conjugate and Cationic Lipids

Figure 6:
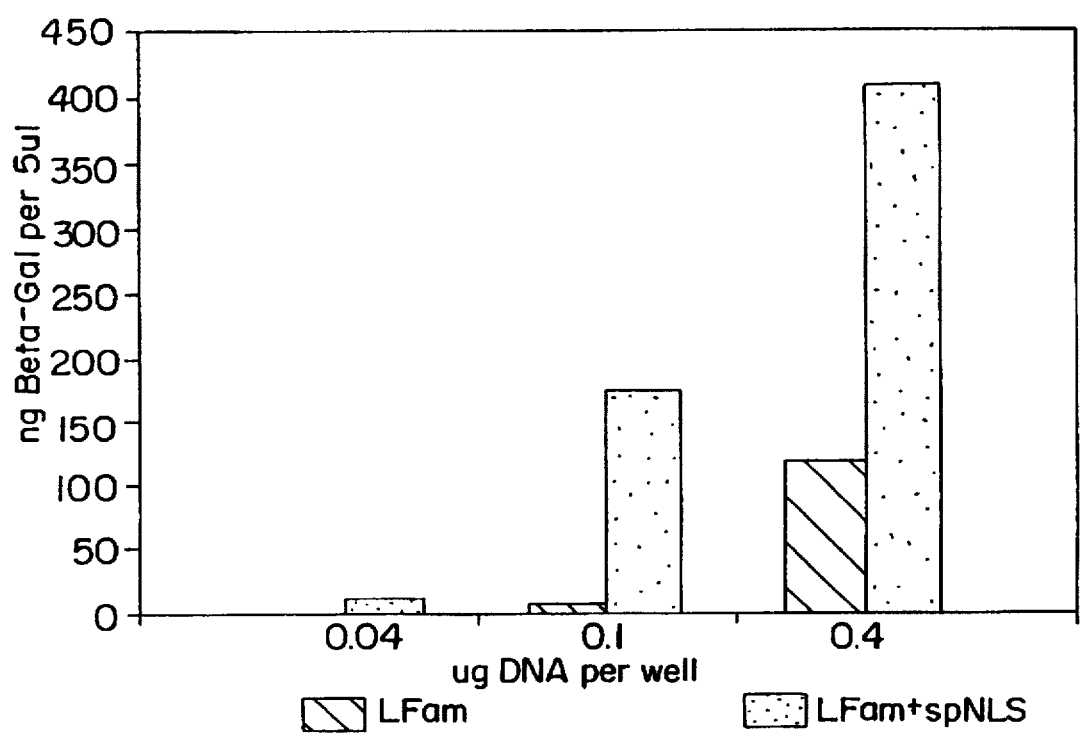
FIG. 6 is a bar graph showing the effect of concentration of spermine-NLS-DNA complexes on enhancement of transfection of BHK-21 cells.
Figure 8A:
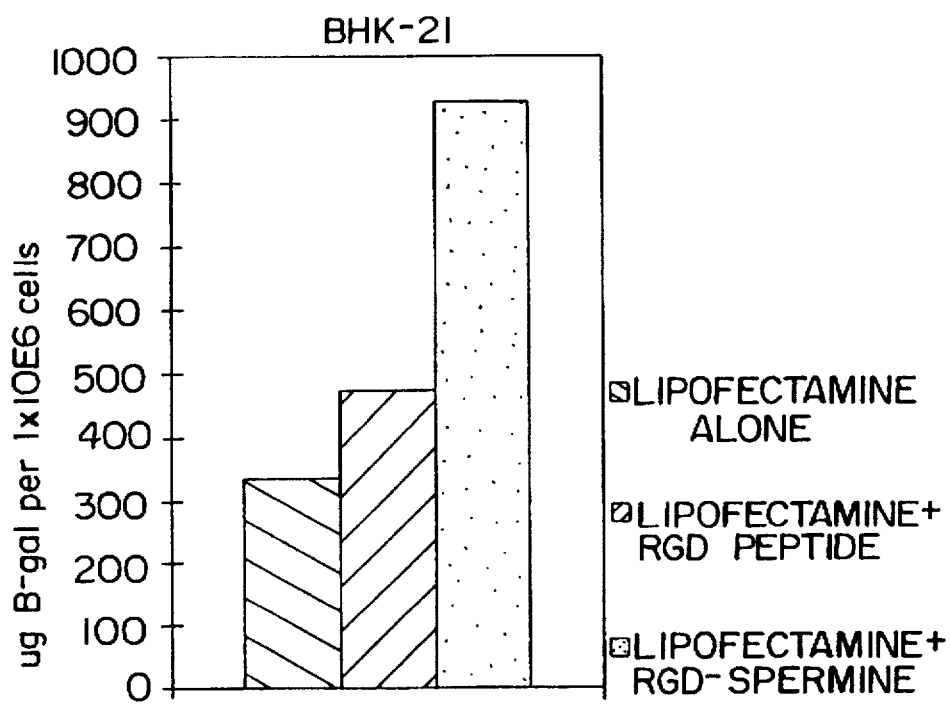
FIG. 8 is a set of bar graphs showing the effect in concentration of RGD-spermine peptide on "LIPOFECTAMINE"-mediated transfection of adherent cells. The graph shows peak expression points.
Figure 8B:
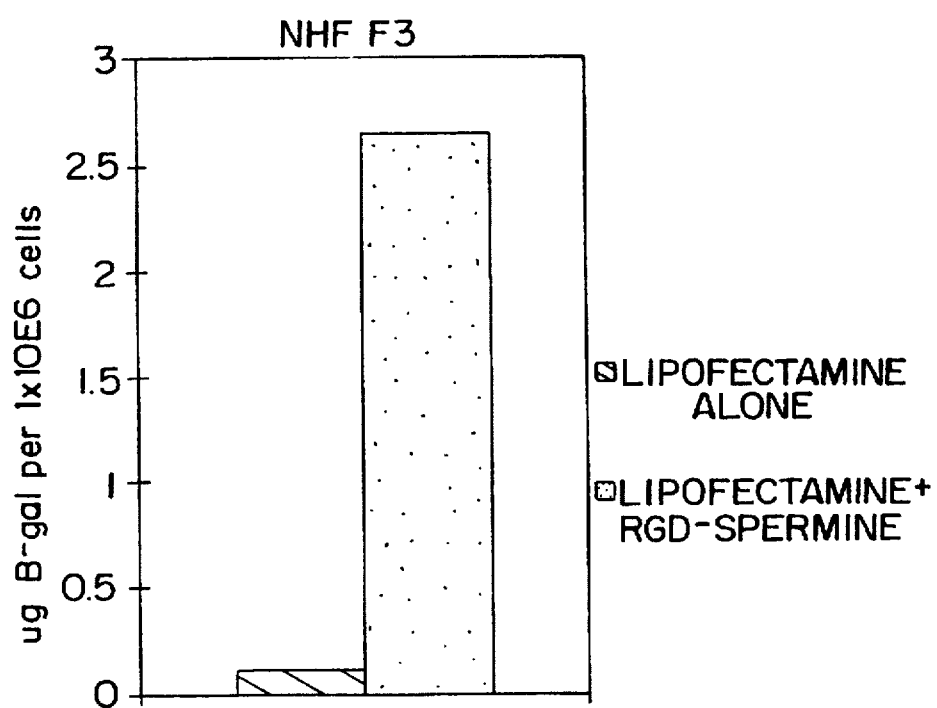
Figure 8C:
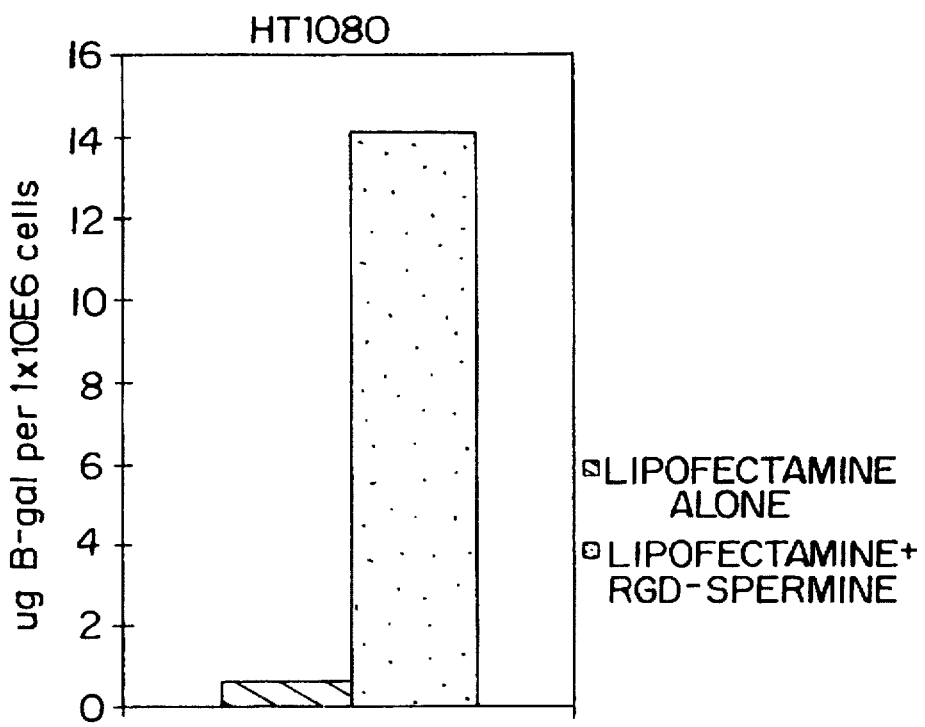
Figure 8D:
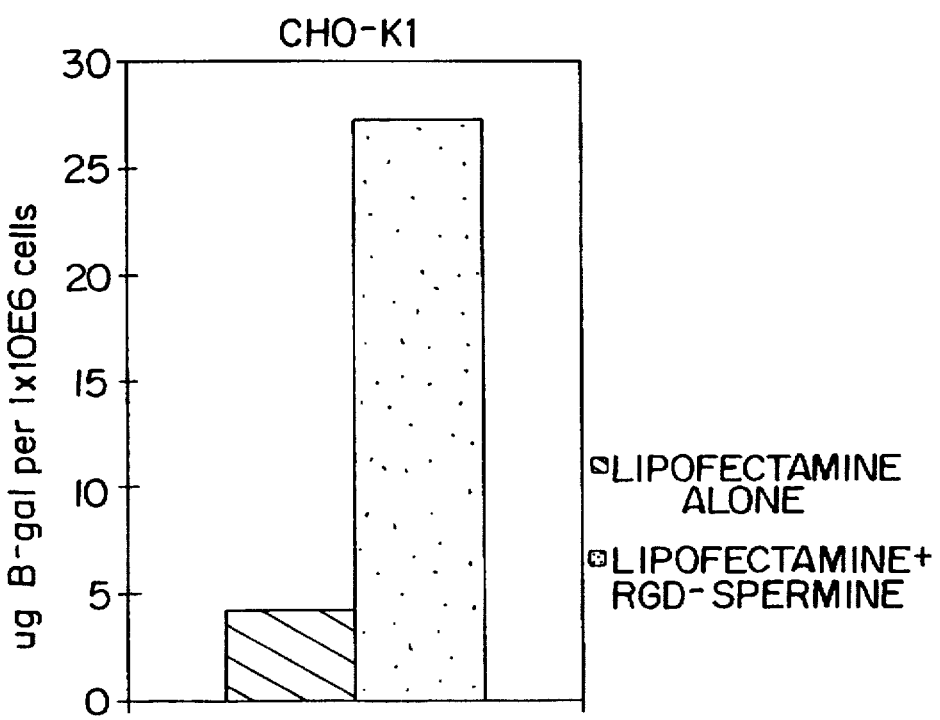
Figure 8E:
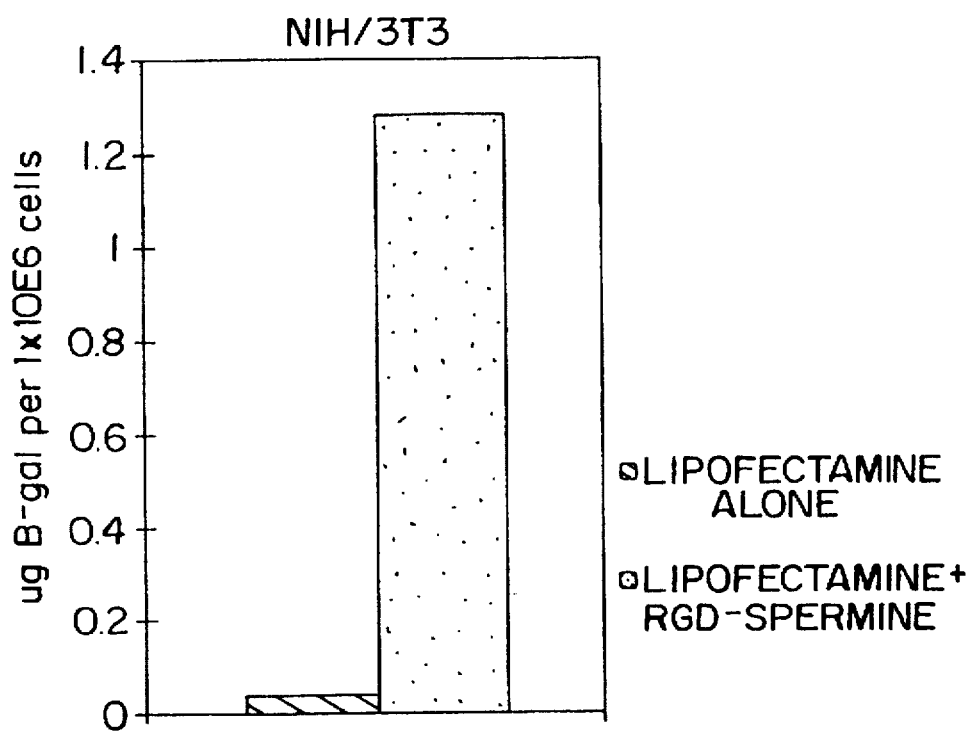

The spermine-NLS peptide was synthesized as described in Example 2. Transfection protocols were as described in Example 3, except that the concentration of the complexes was varied. BHK-21 cells were plated the day before transfection at 2×10⁴ per well on a 24-well dish. Before transfection, cells were rinsed with serum-free DMEM. Each well was fed with 0.25 mL serum-free DMEM transfection medium. Two 25 μl aliquots of "OPTI-MEM"-I medium were prepared, one containing 3 μg "LIPOFECTAMINE" and the second containing 0.4 μg pCMVβgal DNA. Spermine-peptide conjugates were dissolved in water at 25-fold their final concentration. 10 μl peptide was added to the "OPTI-MEM"-DNA aliquot and incubated for 15 minutes at room temperature. The "LIPOFECTAMINE" solution was added to the DNA-peptide solution, and incubated 30 minutes at room temperature to allow complex formation. 50 μl of full-strength complexes and complexes diluted 1:4 and 1:10 were added to each well. After approximately 5 hours incubation at 37° C., one mL DMEM containing 13% (v/v) FBS was added. The next day cells were harvested, lysed and lysed cell extracts were assayed for β-galactosidase activity, as described in Example 4. The results are shown in FIG. 6. FIG. 6 shows the peak expression levels over a dose-response range for the diluted complexes. As shown in FIG. 6, pre-complexing spermine-NLS to DNA prior to formation of complexes with the lipid transfection reagent allows enhanced transfection with less total DNA.

Example 11

Transfection of BHK-21 Cells Using Spermine-VSVG Conjugate and Cationic Lipids

Figure 7:
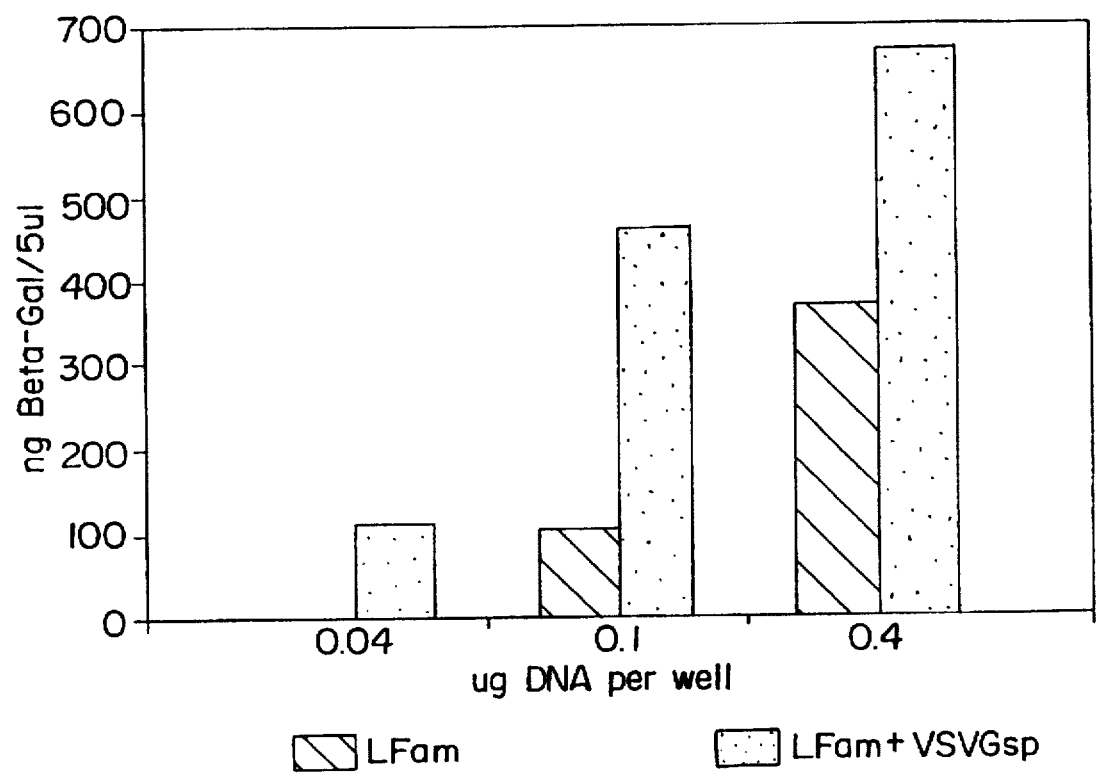
FIG. 7 is a bar graph showing the effect of concentration of spermine-VSVG-DNA complex on enhancement of transfection of BHK-21 cells.

The spermine-VSVG peptide was synthesized as described in Example 2. Transfection protocols were as described in Example 3, except that the concentration of the complexes was varied. BHK-21 cells were plated the day before transfection at 2×10⁴ per well on a 24-well dish. Before transfection, cells were rinsed with serum-free DMEM. Each well was fed with 0.25 mL serum-free DMEM transfection medium. Two 25 μl aliquots of "OPTI-MEM"-I medium were prepared, one containing 3 μg "LIPOFECTAMINE" and the second containing 0.4 μg pCMVβgal DNA. Spermine-VSVG conjugates were dissolved in water at 25-fold their final concentration. 20 μl peptide was added to the "OPTI-MEM"-DNA aliquot and incubated for 15 minutes at room temperature. The "LIPOFECTAMINE" solution was added to the DNA-peptide solution, and incubated 30 minutes at room temperature to allow complex formation. 50 μl of full-strength complexes and complexes diluted 1:4 and 1:10 were added to each well. After approximately 5 hours incubation at 37° C., one mL DMEM containing 10% (v/v) FBS was added. The next day cells were harvested, lysed and lysed cell extracts were assayed for β-galactosidase activity, as described in Example 4. The results are shown in FIG. 7. FIG. 7 shows the peak expression levels over a dose-response range for the diluted complexes. As shown in FIG. 7, pre-complexing spermine-VSVG to DNA prior to formation of complexes with the lipid transfection reagent allows enhanced transfection with less total DNA.

Example 12

Transfection of BHK-21, HT1080, CHO-K1, NIH/3T3 and Human fibroblasts (HPF) using RGD-spermine peptide For transfection, cells were trypsinized the day prior to treatment and replated at 6×10⁴ cells per well in 24-well Falcon plates. Cells were rinsed once with serum-free DMEM prior to transfection and 0.25 mL of serum-free DMEM+non-essential amino acids (NEAA) was added to each well. Plasmid DNA was diluted to 8.0 µg/mL in "OPTI-MEM"-I (Gibco/BRL: Life Technologies, Inc., Gaithersburg, Md.). To each well, 25 µL of diluted DNA was added to appropriate wells of a sterile round bottom 96 well Costar plate. To appropriate wells, various concentrations of RGD-spermine peptide (0-12µg/well) were allowed to complex with DNA for 30 minutes at room temperature. The sequence of the RGD-spermine peptide is as follows: GRGDSPC-spermine. "LIPOFECTAMINE" (GIBCO/BRL: Life Technologies, Inc.) was separately diluted into "OPTI-MEM"-I (0-1.5 µL), and allowed to incubate for 10 minutes at room temperature. "LIPOFECTAMINE" is a 3:1 (w/w) mixture of the polycationic lipid, 2,3-dioleyloxy-N-[2 (sperminecarboxamido)ethyl]-N,N-dimethyl-1-propanaminumtrifluoroacetate (DOSPA), and DOPE. After this pre-incubation period, equal volumes of the diluted transfection reagent were gently mixed with the diluted peptide-DNA complex mixture. The reaction mixture was incubated at room temperature for 30 minutes to form peptide-DNA-lipid aggregates. The aggregates were then transferred to the appropriate wells of the 24-well plates containing 0.25 mL serum-free DMEM +NEAA; cells were incubated at 37° C. After approximately 5 hours, 1 mL modified growth media (DMEM+NEAA+13% FBS, for NIH/3T3 cells DMEM+NEAA+13% calf serum) was added to each well. Cells were assayed the next day for β-galactosidase activity as described in Example 4.

The results are shown in FIG. 8 which demonstrates the peak expression levels in various adherent cell lines. Relative fold enhancement over "LIPOFECTAMINE" alone are shown in Table 4.

Example 13

Transfection of Jurkat and K562 cells using RGD-spermine enhancement peptide

Plasmid DNA was diluted to 8 µg/mL in "OPTI-MEM"-I (Gibco/BRL: Life Technologies, Inc., Gaithersburg, Md.). In separate microcentrifuge tubes, 100 µL of diluted DNA was added to appropriate tubes. To each tube, either 0 or 12 µg of RGD-spermine peptide was added and allowed to incubate for 30 minutes at room temperature. To appropriate wells of a 24-well plate, 0.1 mL "OPTI-MEM"-I reduced serum medium and either 0.4 of 0.8 µof "LIPO-FECTAMINE" reagent were added, and incubated at room temperature for 10 minutes. Simultaneously, cells were counted, collected, and rinsed with "OPTI-MEM"-I prior to transfection. In order to form peptide-DNA-lipid complexes, contents of the microfugetubes were transferred to appropriate wells of the plate and incubated for 30 minutes at room temperature. To each well, 40 µL of cell suspension containing 4×10$^5$ cells in "OPTI-MEM"-I was added and incubated at 37° C. After approximately 4 hours, 0.4 mL of growth media (RPMI 1640+15% FBS) was added to each well. For Jurkat cells, PHA (phytahemagglutinin, Sigma) and PMA (Phorbol myristate acetate, Sigma) at final concentrations of µ/mL and 50 mg/mL, respectively, were added to the medium after transfection to enhance promoter activity and gene expression. K562 cells only required PMA for enhancement of promoter activity.

To quantitate the amount of β-galactosidase expressed by transfected cells, cells were harvested directly in 0.1M Tris-HCL pH 8.0 containing 0.1% "TRITON" X-100. Cell extracts were cleared by centrifugation and aliquots were assayed as described in Example 4, using ONPG substrate.

Figure 9A:
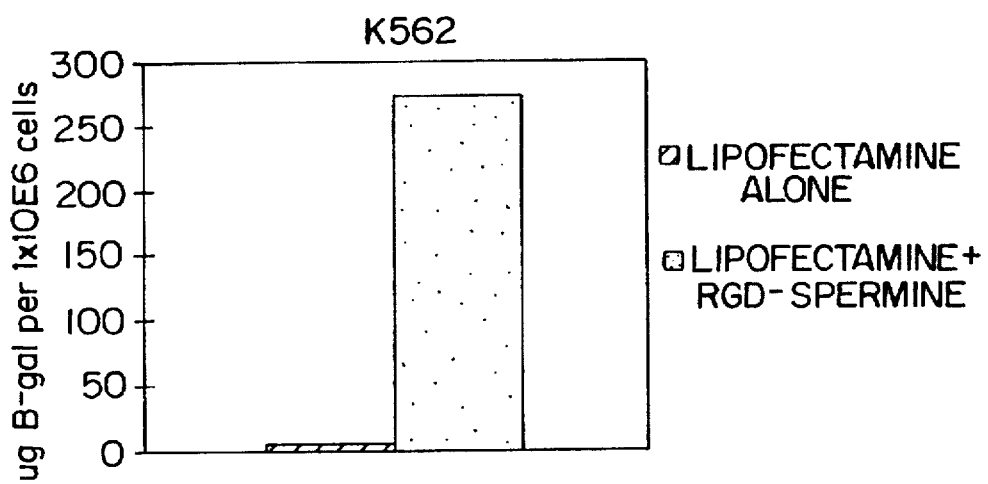
FIG. 9 is a bar graph showing the effect in concentration of RGD-spermine peptide on "LIPOFECTAMINE"-mediated transfection of Jurkat and K562 cells. The graph shows peak expression points.
Figure 9B:
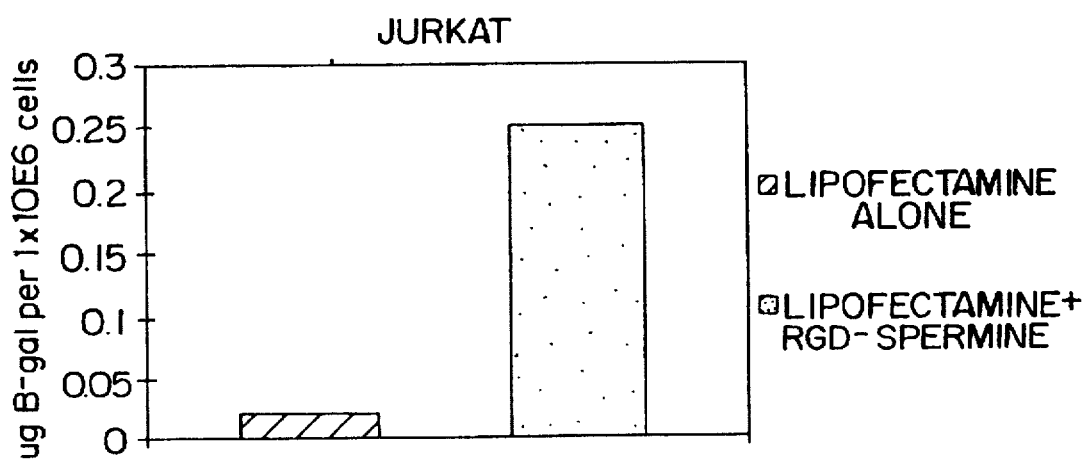

The results are shown in FIG. 9 which demonstrates the peak expression levels in the suspension cell lines, K562 and Jurkat cells. Relative fold enhancement over "LIPO-FECTAMINE" alone are also shown in Table 4.

TABLE 4

Relative fold enhancement of transfection with RGD-spermine and "LIPOFECTAMINE" over "LIPOFECTAMINE" alone, in various cell lines

| Cell Line | Enhancement over "LIPOFECTAMINE" alone |
|---|---|
| BHK-21 | ~3 fold |
| HT1080 | ~31 fold |
| NIH/3T3 | ~1-2 fold |
| CHO-K1 | ~7 fold |
| Human fibroblasts | ~24 fold |
| Jurkat | ~12 fold |
| K562 | ~51 fold |

We claim:

1. A composition for transfecting a eukaryotic cell produced by first forming a composition comprising a peptide-nucleic acid complex, followed by addition of a cationic lipid capable of aggregating said peptide-nucleic acid complex to said complex-containing composition wherein said peptide comprises a nuclear localization signal sequence, or an RGD peptide sequence.

2. The composition of claim 1 wherein said peptide is a nuclear localization signal peptide, or comprises an RGD peptide sequence.

3. The composition of claim 1 wherein said peptide is a mixture of two or more peptides.

4. The composition of claim 1 wherein said peptide comprises an RGD peptide sequence.

5. The composition of claim 1 wherein said peptide comprises a nuclear localization signal sequence.

6. The composition of claim 1 wherein said nuclear localization signal sequence is derived from a simian virus 40.

7. The composition of claim 6 wherein said nuclear localization signal sequence is derived from the SV40 large T antigen.

8. The composition of claim 1 wherein said peptide binds to a binding site on the surface of a cell optionally inducing endocytosis of the whole complex.

9. The composition of claim 1 wherein said peptide is a cell adhesion peptide comprising an RGD peptide.

10. The composition of claim 1 wherein said cationic lipid is a polyvalent cationic lipid.

11. The composition of claim 10 wherein said polyvalent cationic lipid is 2,3-dioleyloxy-N-[2(sperminecarboxamido)ethyl]- N,N-dimethyl-1-propanaminium trifluoroacetate.

12. The composition of claim 1 wherein after said peptide-nucleic acid-complex is formed, it is added to a mixture of a cationic lipid and a neutral lipid.

13. The composition of claim 12 wherein said neutral lipid is dioleoylphosphatidylethanolamine.

14. A composition for transfecting a eukaryotic cell which comprises a peptide-nucleic acid complex, wherein said peptide is conjugated to a DNA binding group, and a cationic lipid capable of aggregating said peptide-nucleic acid complex.

15. The composition of claim 14 wherein said DNA binding group is a polyamine.

16. The composition of claim 15 wherein said polyamine is spermine.

17. The composition of claim 16 wherein said peptide is a K5 peptide or an E5 peptide of a hemagglutinin.

18. The composition of claim 16 wherein said peptide comprises a nuclear localization signal sequence.

19. The composition of claim 16 wherein said peptide comprises a VSVG peptide sequence.

20. The composition of claim 16 wherein said peptide comprises an RGD peptide sequence.

21. The composition of claim 14 wherein said peptide is a cell adhesion-peptide comprising a RGD peptide sequence.

22. The composition of claim 14 wherein said cationic lipid is a polyvalent cationic lipid.

23. The composition of claim 22 wherein said polyvalent cationic lipid is 2,3-dioleyloxy-N-[2(sperminecarboxamido)ethyl]-N,N-dimethyl-1-propanaminium trifluoroacetate.

24. The composition of claim 14 further comprising a neutral lipid.

25. The composition of claim 24 wherein said neutral lipid is dioleoyl phosphatidylethanolamine.

26. The composition of claim 14 wherein said peptide comprises a nuclear localization signal sequence.

27. The composition of claim 14 wherein said peptide comprises an NLS peptide sequence, a VSVG peptide sequence, an E5 peptide sequence, a K5 peptide or an RGD peptide sequence.

28. The composition of claim 27 wherein said peptide comprises nuclear localization signal sequence derived from a simian virus 40.

29. The composition of claim 28 wherein said peptide comprises nuclear localization signal sequence derived from the SV40 large T antigen.

30. The composition of claim 14 wherein said peptide is an NLS peptide, a VSVG peptide, or comprises an RGD peptide sequence.

31. The composition of claim 14 wherein said peptide comprises a VSVG peptide sequence.

32. The composition of claim 14 wherein said peptide comprises an RGD peptide sequence.

33. The composition of claim 14 wherein said peptide comprises an E5 peptide sequence or a K5 peptide sequence.

34. The composition of claim 14 wherein said peptide is a mixture of two or more peptides.

* * * * *

UNITED STATES PATENT AND TRADEMARK OFFICE
CERTIFICATE OF CORRECTION

PATENT NO. : 5,736,392

DATED : Apr. 7, 1998

INVENTOR(S) : Hawley-Nelson et al.

It is certified that error appears in the above-identified patent and that said Letters Patent is hereby corrected as shown below:

Column 2, line 21, replace "HA-2N-terminal" with --HA-2 N-terminal--.
Column 2, line 27, replace "vira" with --viral--.

Column 4, line 51, replace "vital" with --viral--.
Column 5, line 14, add "can be made" after "cells".
Column 7, line 4, delete "amino acids," and replace with --amino acids),--.
Column 7, line 23, delete "equivalent" and replace with --equivalents--.
Column 8, line 45, delete "Naturally," and replace with --Naturally--. Column 10, line 27, delete "is" and replace with --are--.
Column 12, line 31, delete "phosphotidyletahnolamine" and replace with --phosphotidylethanolamine--.
Column 12, line 37, add "," after ")"
Column 18, line 22, add "on" after "Mixtures" in the title to Example 7. Column 21, line 48, replace "0.8 µof" with --0.8 µg of--.
Column 22, line 5, replace "microfugetubes" with --microcentrifuge--.
Claim 6, replace "1" with --5--.
Claim 25, remove the space after "dioleoyl".
Claim 28, add "a" after "comprises".
Claim 29, add "a" after "comprises".

Signed and Sealed this

Fifteenth Day of December, 1998

Attest:

BRUCE LEHMAN

*Attesting Officer*   Commissioner of Patents and Trademarks

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: Not Relevant ( i i ) MOLECULE TYPE: peptide ( i i i ) HYPOTHETICAL: NO ( x i ) SEQUENCE DESCRIPTION: SEQ ID NO:1:

Gly Leu Phe Glu Ala Ile Ala Glu Phe Ile Glu Gly Gly Trp Glu Gly
1               5                       10                      15
Leu Ile Glu Gly
         20

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:2:

Gly Leu Phe Lys Ala Ile Ala Lys Phe Ile Lys Gly Gly Trp Lys Gly
1               5                       10                      15
Leu Ile Lys Gly
         20

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:3:

Gly Leu Phe Gly Ala Ile Ala Gly Phe Ile Glu Asn Gly Trp Glu Gly
1               5                       10                      15
Met Ile Asp Gly
         20

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:4:

Lys Phe Thr Ile Val Phe
1               5

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:5:

Gly Tyr Gly Pro Lys Lys Lys Arg Lys Val Gly Gly
1               5                           10

( 2 ) INFORMATION FOR SEQ ID NO:6:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i x ) FEATURE:
      ( A ) NAME/KEY: Modified-site
      ( B ) LOCATION: 1..13
      ( D ) OTHER INFORMATION: /product="cysteine"
        / label= modified
        / note= "The C-terminal cysteine is covalently modified by conjugation to spermine."

( x i ) SEQUENCE DESCRIPTION: SEQ ID NO:6:

Gly Tyr Gly Pro Lys Lys Lys Arg Lys Val Gly Gly Cys
1               5                           10

( 2 ) INFORMATION FOR SEQ ID NO:7:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i x ) FEATURE:
      ( A ) NAME/KEY: Modified-site
      ( B ) LOCATION: 1..10
      ( D ) OTHER INFORMATION: /product="cysteine"
        / label= modified
        / note= "The C-terminal cysteine is modified by covalent conjugation to sperimine."

( x i ) SEQUENCE DESCRIPTION: SEQ ID NO:7:

Pro Lys Lys Lys Arg Lys Val Gly Gly Cys
1               5                   10

( 2 ) INFORMATION FOR SEQ ID NO:8:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i x ) FEATURE:
      ( A ) NAME/KEY: Modified-site
      ( B ) LOCATION: 1..13
      ( D ) OTHER INFORMATION: /product="cysteine"
        / label= modified
        / note= "The N-terminal cysteine is modified by covalent conjugation to spermine."

( x i ) SEQUENCE DESCRIPTION: SEQ ID NO:8:

```
Cys  Gly  Tyr  Gly  Pro  Lys  Lys  Lys  Arg  Lys  Val  Gly  Gly
1                  5                         10
```

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (iii) HYPOTHETICAL: NO (ix) FEATURE:
        (A) NAME/KEY: Modified-site
        (B) LOCATION: 1..7
        (D) OTHER INFORMATION: /product="cysteine"
            / label= modified
            / note= "The C-terminal cysteine is modified by covalent
            conjugation to spermine."

(xi) SEQUENCE DESCRIPTION: SEQ ID NO:9:

```
Lys  Phe  Thr  Ile  Val  Phe  Cys
1                  5
```

(2) INFORMATION FOR SEQ ID NO:10:

(i) SEQUENCE CHARACTERISTICS:
        (A) LENGTH: 7 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:10:

```
Gly  Arg  Gly  Asp  Ser  Pro  Cys
1                  5
```

(2) INFORMATION FOR SEQ ID NO:11:

(i) SEQUENCE CHARACTERISTICS:
        (A) LENGTH: 6 amino acids
        (B) TYPE: amino acid
        (C) STRANDEDNESS: single
        (D) TOPOLOGY: Not Relevant (ii) MOLECULE TYPE: protein (iii) HYPOTHETICAL: NO (v) FRAGMENT TYPE: internal (xi) SEQUENCE DESCRIPTION: SEQ ID NO:11:

```
Arg  Gly  Asp  Ser  Pro  Cys
1                  5
```

(2) INFORMATION FOR SEQ ID NO:12:

(i) SEQUENCE CHARACTERISTICS:
        (A) LENGTH: 4 amino acids
        (B) TYPE: amino acid
        (C) STRANDEDNESS: single
        (D) TOPOLOGY: Not Relevant (ii) MOLECULE TYPE: protein (iii) HYPOTHETICAL: NO ( v ) FRAGMENT TYPE: internal ( x i ) SEQUENCE DESCRIPTION: SEQ ID NO:12:

Arg Glu Asp Val
1

( 2 ) INFORMATION FOR SEQ ID NO:13:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: Not Relevant ( i i ) MOLECULE TYPE: protein ( i i i ) HYPOTHETICAL: NO ( v ) FRAGMENT TYPE: internal ( x i ) SEQUENCE DESCRIPTION: SEQ ID NO:13:

Arg Gly Asp Val
1

( 2 ) INFORMATION FOR SEQ ID NO:14:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: Not Relevant ( i i ) MOLECULE TYPE: protein ( i i i ) HYPOTHETICAL: NO ( v ) FRAGMENT TYPE: internal ( x i ) SEQUENCE DESCRIPTION: SEQ ID NO:14:

Arg Gly Asp Asn
1

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: Not Relevant ( i i ) MOLECULE TYPE: protein ( i i i ) HYPOTHETICAL: NO ( v ) FRAGMENT TYPE: internal ( x i ) SEQUENCE DESCRIPTION: SEQ ID NO:15:

Arg Gly Asp Met
1

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: Not Relevant ( i i ) MOLECULE TYPE: protein ( i i i ) HYPOTHETICAL: NO ( v ) FRAGMENT TYPE: internal ( x i ) SEQUENCE DESCRIPTION: SEQ ID NO:16:

Arg Gly Asp Thr
1

( 2 ) INFORMATION FOR SEQ ID NO:17:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: Not Relevant ( i i ) MOLECULE TYPE: protein ( i i i ) HYPOTHETICAL: NO ( v ) FRAGMENT TYPE: internal ( i x ) FEATURE:
        ( A ) NAME/KEY: Region
        ( B ) LOCATION: 1..4
        ( D ) OTHER INFORMATION: /note= "Xaa at position 4 can be
        various amino acids."

( x i ) SEQUENCE DESCRIPTION: SEQ ID NO:17:

Arg Gly Asp Xaa
1

( 2 ) INFORMATION FOR SEQ ID NO:18:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: Not Relevant ( i i ) MOLECULE TYPE: protein ( i i i ) HYPOTHETICAL: NO ( v ) FRAGMENT TYPE: internal ( x i ) SEQUENCE DESCRIPTION: SEQ ID NO:18:

Arg Gly Asp Ser
1

( 2 ) INFORMATION FOR SEQ ID NO:19:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: Not Relevant ( i i ) MOLECULE TYPE: protein ( i i i ) HYPOTHETICAL: NO ( v ) FRAGMENT TYPE: internal ( x i ) SEQUENCE DESCRIPTION: SEQ ID NO:19:

Arg Gly Asp Ala
1

( 2 ) INFORMATION FOR SEQ ID NO:20:

( i ) SEQUENCE CHARACTERISTICS:
        ( A ) LENGTH: 25 amino acids
        ( B ) TYPE: amino acid -continued

```
( C ) STRANDEDNESS: single
( D ) TOPOLOGY: Not Relevant ( i i ) MOLECULE TYPE: peptide ( i i i ) HYPOTHETICAL: NO ( x i ) SEQUENCE DESCRIPTION: SEQ ID NO:20:

Asp Glu Leu Pro Gln Leu Val Thr Leu Pro His Pro Asn Leu His Gly
  1               5                   10                  15

Pro Glu Ile Leu Asp Val Pro Ser Thr
              20                  25

( 2 ) INFORMATION FOR SEQ ID NO:21:

( i ) SEQUENCE CHARACTERISTICS:
          ( A ) LENGTH: 10 amino acids
          ( B ) TYPE: amino acid
          ( C ) STRANDEDNESS: single
          ( D ) TOPOLOGY: Not Relevant ( i i ) MOLECULE TYPE: protein ( i i i ) HYPOTHETICAL: NO ( v ) FRAGMENT TYPE: internal ( x i ) SEQUENCE DESCRIPTION: SEQ ID NO:21:

His Ala Ile Arg Gly Gly Thr Phe Ala Thr
  1               5                   10
```